(12) United States Patent
Aon et al.

(10) Patent No.: US 11,602,488 B2
(45) Date of Patent: Mar. 14, 2023

(54) CONNECTED PILL DISPENSER

(71) Applicant: Projit Aon, Martinsville, NJ (US)

(72) Inventors: Projit Aon, Martinsville, NJ (US);
Ashok Rakhit, Warren, NJ (US);
Edward G. Solomon, Menlo Park, CA (US)

(73) Assignee: NUCLEUSRX LLC, Martinsville, NJ (US)

( * ) Notice: Subject to any disclaimer, the term of this patent is extended or adjusted under 35 U.S.C. 154(b) by 0 days.

(21) Appl. No.: 16/863,955

(22) Filed: Apr. 30, 2020

(65) Prior Publication Data
US 2020/0345587 A1    Nov. 5, 2020

Related U.S. Application Data

(60) Provisional application No. 62/841,211, filed on Apr. 30, 2019.

(51) Int. Cl.
| | |
|---|---|
| *A61J 7/00* | (2006.01) |
| *A61J 1/03* | (2023.01) |
| *G05B 19/042* | (2006.01) |
| *G16H 40/67* | (2018.01) |
| *G16H 20/13* | (2018.01) |

(Continued)

(52) U.S. Cl.
CPC ............... *A61J 7/0076* (2013.01); *A61J 1/03* (2013.01); *B65G 61/00* (2013.01); *G05B 19/042* (2013.01); *G16H 10/60* (2018.01); *G16H 20/13* (2018.01); *G16H 40/67* (2018.01); *G16H 50/20* (2018.01); *G16H 50/50* (2018.01); *G16H 70/40* (2018.01); *A61B 5/0077* (2013.01); *A61B 5/021* (2013.01); *A61B 5/1118* (2013.01); *A61B 5/4839* (2013.01);

(Continued)

(58) Field of Classification Search
CPC ... G16H 20/13; G07F 17/0092; A61J 2200/30
USPC .................................................. 700/231–244
See application file for complete search history.

(56) References Cited

U.S. PATENT DOCUMENTS

| | | | |
|---|---|---|---|
| 5,642,731 A * | 7/1997 | Kehr ....................... | G07F 11/62 |
| | | | 600/300 |
| 5,812,410 A | 9/1998 | Lion et al. | |

(Continued)

*Primary Examiner* — Timothy R Waggoner
(74) *Attorney, Agent, or Firm* — Dentons Cohen & Grigsby P.C.

(57) ABSTRACT

Apparatus and associated methods relate to a connected pill dispenser configured to treat a patient's illness with a robotic arm adapted to deliver a prescribed medication dose to a patient in their home, analyze the patient's response to the dose based on various sensor inputs, automatically determine whether the patient took the medicine and send the provider the result of providing the medication dose to the patient. In an illustrative example, the patient may be a chronic, acute, or terminal illness patient. The medication dose may be, for example, a medication prescribed by a doctor to be taken in a specific amount at specific times. In some embodiments, the connected pill dispenser may automatically notify the patient when a medication dose is due. Various embodiments may determine if the patient consumed a medication dose based on machine vision, audio, or other sensor data, permitting caregiver notification of patient medication adherence, medication compliance, or non-adherence and sensor inputs as data on potential effectiveness and/or side effects.

28 Claims, 18 Drawing Sheets

(51) Int. Cl.
*G16H 10/60* (2018.01)
*G16H 50/20* (2018.01)
*G16H 50/50* (2018.01)
*G16H 70/40* (2018.01)
*B65G 61/00* (2006.01)
*A61B 5/021* (2006.01)
*A61B 5/11* (2006.01)
*A61B 5/00* (2006.01)

(52) U.S. Cl.
CPC ........ *A61J 2200/30* (2013.01); *A61J 2200/70* (2013.01); *G05B 2219/25257* (2013.01)

(56) References Cited

U.S. PATENT DOCUMENTS

| | | |
|---|---|---|
| 5,927,545 A | 7/1999 | Pearson |
| 6,256,967 B1 | 7/2001 | Hebron et al. |
| 6,471,087 B1 * | 10/2002 | Shusterman ........... G16H 20/13 221/2 |
| 6,717,598 B1 | 4/2004 | Melton, Jr. et al. |
| 7,122,005 B2 | 10/2006 | Shusterman |
| 7,530,211 B2 | 5/2009 | McErlean et al. |
| 7,828,147 B2 | 11/2010 | Caracciolo et al. |
| 8,061,109 B2 | 11/2011 | Freudelsperger |
| 8,600,548 B2 | 12/2013 | Bossi et al. |
| D733,454 S | 7/2015 | Von Heifner et al. |
| 9,073,206 B2 | 7/2015 | Carson et al. |
| 9,271,897 B2 | 3/2016 | Costello et al. |
| 9,358,499 B2 | 6/2016 | Akdogan et al. |
| 9,400,873 B2 | 7/2016 | Kamen et al. |
| 9,721,418 B2 | 8/2017 | van Ooyen et al. |
| 9,731,853 B2 | 8/2017 | Akdogan et al. |
| 10,025,908 B1 * | 7/2018 | Orellano ................ G16H 40/67 |
| 10,179,411 B2 | 1/2019 | Lessing et al. |
| 10,246,207 B2 | 4/2019 | Holmes |
| 10,282,521 B2 | 5/2019 | Hanson et al. |
| 10,297,032 B2 | 5/2019 | Hanina et al. |
| 10,360,751 B2 | 7/2019 | Berg et al. |
| 2002/0104848 A1 * | 8/2002 | Burrows ................ A61M 5/002 221/1 |
| 2007/0185615 A1 * | 8/2007 | Bossi ................... G07F 17/0092 700/244 |
| 2009/0299522 A1 | 12/2009 | Savir et al. |
| 2010/0121315 A1 * | 5/2010 | Trovato ................ H04L 9/3278 604/890.1 |
| 2010/0256808 A1 * | 10/2010 | Hui ..................... G07F 11/1657 700/225 |
| 2011/0201421 A1 * | 8/2011 | De Oliveira .......... G16H 20/13 463/30 |
| 2016/0117484 A1 | 4/2016 | Hanina et al. |
| 2016/0136054 A1 * | 5/2016 | Bunker ................ A61J 7/0084 340/573.1 |
| 2016/0162660 A1 * | 6/2016 | Strong .................. A61J 7/0076 700/236 |
| 2017/0020785 A1 | 1/2017 | McCullough |
| 2017/0132867 A1 * | 5/2017 | Berg ..................... G16H 70/20 |
| 2018/0110441 A1 | 4/2018 | Frank et al. |
| 2019/0027238 A1 | 1/2019 | Hanina et al. |
| 2019/0139640 A1 | 5/2019 | Kamen |
| 2019/0205716 A1 * | 7/2019 | Moshkovitz .......... A61J 7/0418 |
| 2019/0322469 A1 | 10/2019 | Haehnel et al. |

* cited by examiner

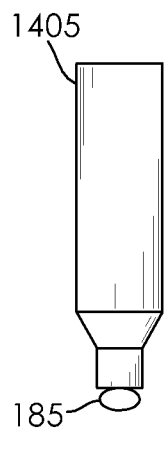 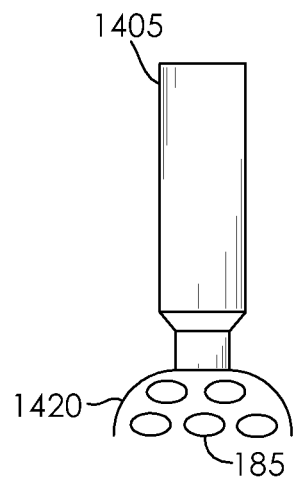 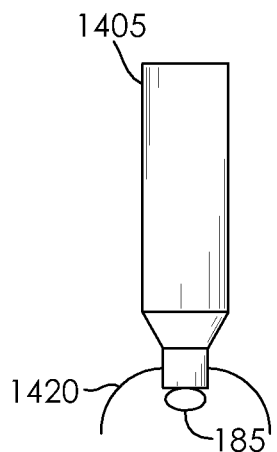 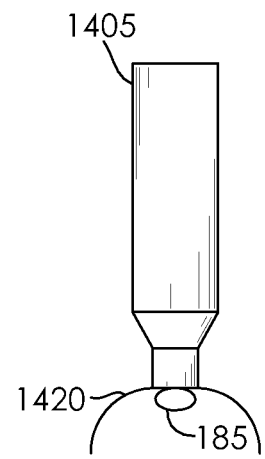
FIG. 15A   FIG. 15B   FIG. 15C   FIG. 15D
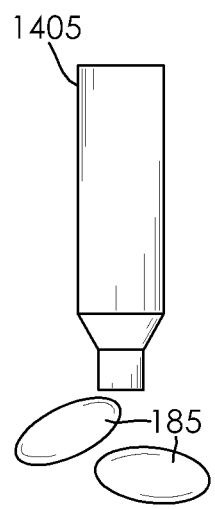 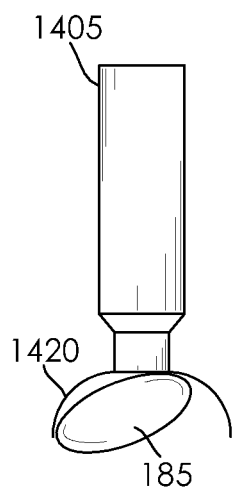 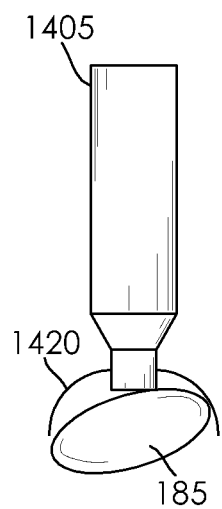 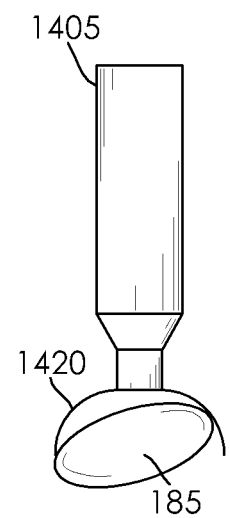
FIG. 15E   FIG. 15F   FIG. 15G   FIG. 15H

CONNECTED PILL DISPENSER

CROSS-REFERENCE TO RELATED APPLICATIONS

This application claims the benefit of U.S. Provisional Application No. 62/841,211, titled "Connected Pill Dispenser," Inventors: Projit Aon and Ashok K. Rakhit; filed by Applicants: Projit Aon and Ashok K. Rakhit, on Apr. 30, 2019.

This application incorporates the entire contents of the above-referenced application herein by reference.

TECHNICAL FIELD

Various embodiments relate generally to chronic, acute, seasonal, or terminal illness patient medication adherence.

BACKGROUND

A chronic illness is an illness that is long-lasting. An acute illness is an illness that may be severe. A patient afflicted with an acute or chronic illness may not find a cure for the condition, even though they are treated by a doctor or hospital. Some patients may receive medical treatment including medication prescribed by a doctor to relieve symptoms or prevent the illness from getting worse. Some patients may need acute or limited time treatment care after release from hospital inpatient treatment, when the patient is still recovering.

Treatment of some illnesses may require timely adherence to multiple therapies on a given day, or drugs that require critical adherence to time of medicine intake because of a narrow therapeutic window to improve efficacy or avoid toxicity. Some patients may experience loss of short term memory (for example, forgetfulness in early dementia, in an elderly or Alzheimer patient), or physically debilitating conditions, and hence, may be dependent on homecare without the benefit of expensive daily licensed nursing services.

Some medication used to treat chronic or acute illness may be expensive. The therapeutic effect of some medicine prescribed to treat a patient's chronic or acute illness may be limited by the patient's adherence to the dosing protocol prescribed by the patient's doctor. Elderly Patients simply taking multiple drugs or patients with debilitating mental or physical illness (for example, diseases like Alzheimer's, Parkinson's, dementia, or multiple sclerosis) may not remember or be physically able to take drugs on time from multiple bottles traditionally dispensed by pharmacies.

In various examples, a patient's adherence to the dosing protocol prescribed by the patient's doctor may be a crucial component of caring for the patient's illness. Lack of adequate medication adherence may result in preventable disease progression and unnecessary cost to payers.

SUMMARY

Apparatus and associated methods relate to a connected pill dispenser configured to treat a patient's illness with a robotic arm adapted to deliver a prescribed medication dose at different times of the day or week to a patient in their home, analyze the patient's response to the dose based on various sensor inputs, automatically determine whether the patient took the medicine, and provide caregivers the result of compliance on intake of medication as well as some response data based on sensor inputs (for example, blood pressure, heart rate, or blood sugar level) as suggested by the prescribing physician. In an illustrative example, the patient may be a chronic illness patient, an acute illness patient, or a patient needing short term treatment during home care for any illness. The medication dose may be, for example, medications prescribed by a doctor to be taken in a specific amount at specific times. In some embodiments, the connected pill dispenser may automatically notify the patient when a medication dose is due. Various embodiments may determine if the patient consumed a medication dose based on machine vision, audio, or other sensor data, permitting caregiver notification of patient medication adherence, medication compliance, or non-adherence. Various designs may advantageously direct the medication adherence, compliance, or non-adherence information to providers (for example, pharmacists, or doctors) and payers (for example, insurance companies, or CMS), in addition to directing the adherence, compliance, and non-adherence information to caregivers.

Various embodiments may achieve one or more advantages. For example, some embodiments may improve a patient's medication adherence. This facilitation may be a result of a system configured to encourage a patient to take the right medication in the right amount at the right time. In some embodiments, a patient's disease treatment outcome may be improved. Such improved treatment outcomes may be a result of more consistent medication dosing provided by a system configured to deliver the prescribed medication to the patient at the time the medication is to be consumed. Some embodiments may reduce the time required for a physician to adjust dosage levels. Such reduced dosage adjustment time may be a result of connecting medication prescribers to real-time patient medication adherence data. In some embodiments, caregivers may be automatically notified of missed doses, permitting rapid caregiver intervention in critical illness care. Such automatic caregiver notification of missed doses may reduce a patient's exposure to undesirable effects due to inconsistent dosing.

Various embodiments may provide caregivers with a real-time patient physical parameter response monitoring capability, permitting a patient to remain at home while receiving care for an acute or chronic illness, or even care during terminal illness. In some designs, the real-time patient physical parameter response monitoring capability may include, for example, measurement and reporting of patient blood pressure, heart rate, blood sugar level, calorie consumption, or other home health monitoring parameters medically advisable or prescribed by a physician. In some embodiments, the effort required to adjust a patient's medication may be reduced, hence reducing drug cost, reduce adverse events, or even optimize overall treatment outcome. Such treatment optimization using real time data may be a result of a connected pill dispenser configured to deliver customized dosages of various medications retained in a variable-access dispensing tray, and sending treatment adherence and associated response data to a physician or pharmacist in time for the next visit, or even treatment interruption if medically necessary. Some embodiments may provide a physician with the capability to adjust doses remotely as per the patient's condition, in the event dynamic or immediate intervention is medically indicated. In various embodiments, a physician's application (mobile or the web portal) may have the capability to set patient-specific parameter thresholds to be notified or alerted automatically. Some embodiments may reduce a pharmacy's inventory cost. This facilitation may be a result of a connected pill dispenser capable of managing pill counts, and generating alerts for the pharmacy to replenish the medication for the patient on time.

The details of various embodiments are set forth in the accompanying drawings and the description below. Other features and advantages will be apparent from the description and drawings, and from the claims.

BRIEF DESCRIPTION OF THE DRAWINGS

FIGS. 15A-15H depict side views of an exemplary connected pill dispenser robotic arm suction grip in various illustrative operational configurations.

To aid understanding, this document is organized as follows. First, illustrative usage of an exemplary connected pill dispenser configured to improve a patient's medication adherence is briefly introduced with reference to FIG. 1. Then, embodiment design examples illustrating hardware, information infrastructure, and networks configured to improve a patient's medication adherence are described with reference to FIGS. 2-10. Finally, with reference to FIGS. 11-20, various embodiment connected pill dispenser component designs are presented to explain improvements in medication adherence technology.

Like reference symbols in the various drawings indicate like elements.

DETAILED DESCRIPTION OF ILLUSTRATIVE EMBODIMENTS

Figure 1:
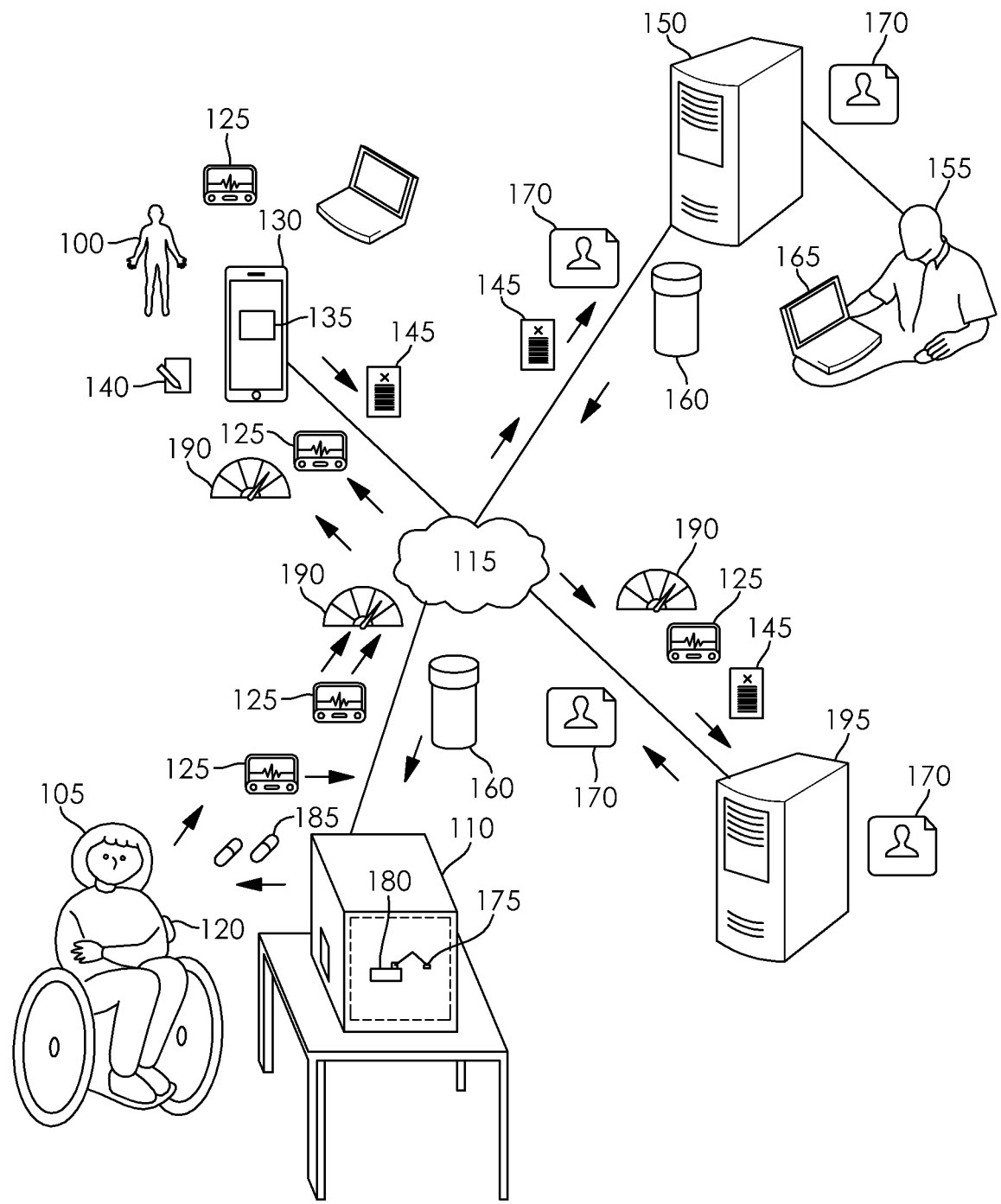
FIG. 1 depicts an illustrative operational scenario wherein a doctor treats an illness of a patient using an exemplary connected pill dispenser configured to treat a patient's illness with a robotic arm adapted to deliver a prescribed medication dose to a patient in their home, analyze the patient's response to the dose based on various sensor inputs, automatically detect with high predictability whether the patient took the medicine, and provide caregivers the result of providing the medication dose to the patient, including a summary of the compliance data.

FIG. 1 depicts an illustrative operational scenario wherein a doctor treats an illness of a patient using an exemplary connected pill dispenser configured to treat a patient's illness with a robotic arm adapted to deliver a prescribed medication dose to a patient in their home, analyze the patient's response to the dose based on various sensor inputs, automatically detect with high predictability whether the patient took the medicine, and provide caregivers the result of providing the medication dose to the patient, including a summary of the compliance data. In FIG. 1, the doctor 100 treats the patient 105 using the exemplary connected pill dispenser 110 via the network cloud 115. In the illustrated embodiment, the patient 105 employs the wearable device 120 configured with sensors adapted to measure patient physical parameters 125. In the depicted embodiment, the wearable device 120 is communicatively and operably coupled with the network cloud 115. In the illustrated embodiment, the wearable device 120 sends the measured patient physical parameters 125 to the doctor's mobile device 130 via the network cloud 115. In the depicted embodiment, the measured patient physical parameters 125 are provided to the doctor's mobile device 130, as well as to doctor's web application accessed by desktop computer. In various designs, the measured patient physical parameters 125 may also be collected at the central server 195. In the depicted embodiment, the mobile device 130 is configured with mobile app 135 adapted to assist the doctor 100 treatment of the patient 105. In the illustrated embodiment, the doctor 100 diagnoses the illness of the patient 105. In the depicted example, the doctor 100 determines the prescription protocol 140 to treat the patient 105 illness. In the illustrated embodiment, the mobile device 130 mobile app 135 creates the prescription 145, based on the prescription protocol 140 determined by the doctor 100. In various embodiments, the prescription 145 may be created/sent by the doctor's web portal. In the depicted embodiment, the mobile app 135 sends the prescription 145 to the pharmacy server 150 communicatively and operably coupled with the network cloud 115. In the illustrated embodiment, the pharmacist 155 issues the prescription 160 using the pharmacy web portal 165 and/or pharmacy mobile app. In the depicted embodiment, the prescription 160 is authorized based on the patient treatment profile data 170. In various embodiments, the patient treatment profile data 170 may include medications or treatments that a payer has authorized for the patient 105. In the illustrated embodiment, the pharmacy 150 server sends the authorized prescription 160 to the connected pill dispenser 110. In the depicted embodiment, the connected pill dispenser 110 robotic arm 175 locates and picks the prescription 160 medication from the dispensing tray 180. In the illustrated embodiment, the connected pill dispenser 110 robotic arm 175 delivers the prescription medication dose 185 to the patient 105. In the depicted embodiment, the connected pill dispenser 110 collaborates with the patient wearable device 120 to determine if the patient 105 consumed the medication dose 185. In various examples, the connected pill dispenser 110 and wearable device 120 may determine if the patient consumed the medication dose 185 based on sensor input, including, for example, image analysis, audio analysis, motion detection, by asking the patient 105 and recording the patient 105 answer, or by measuring patient 105 biological response to the medication dose 185. In various embodiment implementations, several distinct activities may be measured in order to determine compliance/adherence, for example: 1) the patient, or the authorized caregiver, identifies himself/herself using the biometric sensors on the device to begin the dispense action upon a dose reminder; 2) image/video/motion or voice analysis can be performed by the device, correlated with the dispense event to determine a higher degree of compliance; or, 3) biological response collected by patient wearable device 120 correlated with the dispense or the intake event to determine a higher degree of compliance. In the illustrated embodiment, the connected pill dispenser 110 determines the medication adherence score 190 to represent the probability the patient 105 consumed the medication dose 185, based on sensor input. In the depicted embodiment, the connected pill dispenser 110 sends the medication adherence score 190 and related adherence information to the central server 195, which distributes the information to parties that are interested in such information, which may include, for example, the doctor's mobile app, web portal, pharmacy or the payer. In the illustrated embodiment, the doctor 100 mobile app 135 sends the medication adherence score 190, the measured patient physical parameters 125, and the prescription 145, to the payer management server 195. In the depicted embodiment, the payer management server 195 updates the patient treatment profile data 170 based on the real-time medication adherence score 190, the measured patient physical parameters 125, and the prescription 145.

Figure 2:
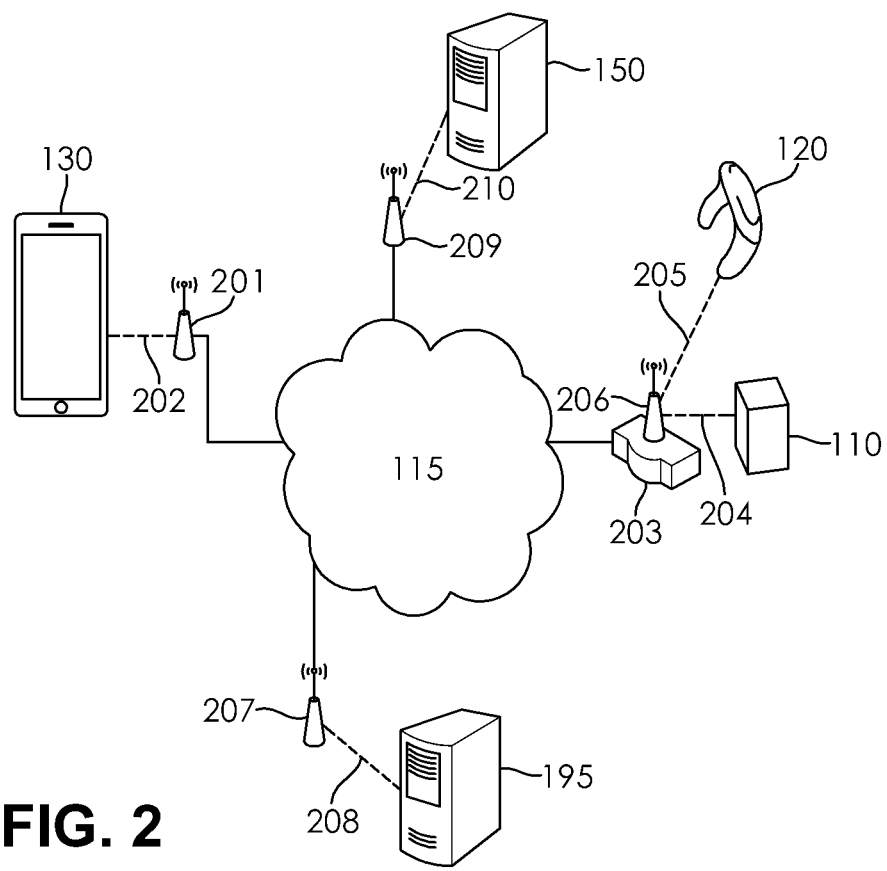
FIG. 2 depicts a schematic view of an exemplary medication adherence network configured to automatically determine whether a patient took a prescribed medicine dose provided by an embodiment connected pill dispenser.

FIG. 2 depicts a schematic view of an exemplary medication adherence network configured to automatically determine whether a patient took a prescribed medicine dose provided by an embodiment connected pill dispenser. In FIG. 2, according to an exemplary embodiment of the present disclosure, data may be transferred to the system, stored by the system and/or transferred by the system to users of the system across local area networks (LANs), wide area networks (WANs), or Wireless WAN (WWAN), such as, for example, cellular networks. In accordance with various embodiments, the system may include numerous servers, data mining hardware, computing devices, or any combination thereof, communicatively connected across one or more LAN, WAN, or WWAN. One of ordinary skill in the art would appreciate that there are numerous manners in which the system could be configured, and embodiments of the present disclosure are contemplated for use with any configuration. Referring to FIG. 2, a schematic overview of a system in accordance with an embodiment of the present disclosure is shown. In the depicted embodiment, an exemplary system includes the exemplary connected pill dispenser 110 configured to improve the patient's medication adherence. In the illustrated embodiment, the connected pill dispenser 110 includes a computing device configured to improve the patient's medication adherence. In the depicted embodiment, the wearable device 120 includes a computing device with sensors adapted to measure patient physical parameters. In the depicted example, the mobile device 130 is a smartphone. In the illustrated example, the pharmacy server 150 is a computing device configured to host and manage data. In the depicted example, the server 195 is a computing device configured to host and manage data. In the illustrated example, the server 195 is the central server that collects information from the connected pill dispenser 110, or prescription from the customer, or prescription configuration from the pharmacists, and feeds information to various parties as and when needed. In various scenarios, the server 195 may be configured to perform a payer management function, in addition to other functions. In various examples, the server 195 could be implemented on a public, private or hybrid cloud infrastructure. In the illustrated embodiment, the mobile device 130 is communicatively and operably coupled by the wireless access point 201 and the wireless link 202 with the network cloud 115 (for example, the Internet) to send, retrieve, or manipulate information in storage devices, servers, and network components, and exchange information with various other systems and devices via the network cloud 115. In the depicted example, the illustrative system includes the router 203 configured to communicatively and operably couple the connected pill dispenser 110 to the network cloud 115 via the communication link 204 and wireless access point 206. In the illustrated example, the router 203 also communicatively and operably couples the wearable device 120 to the network cloud 115 via the communication link 205 and wireless access point 206. In the depicted embodiment, the payer management server 195 is communicatively and operably coupled with the network cloud 115 by the wireless access point 207 and the wireless communication link 208. In the illustrated embodiment, the pharmacy server 150 is communicatively and operably coupled with the network cloud 115 by the wireless access point 209 and the wireless communication link 210. In various examples, one or more of: the connected pill dispenser 110, wearable device 120, mobile device 130, pharmacy server 150, or payer management server 195 may include an application server configured to store or provide access to information used by the system. In various embodiments, one or more application server may retrieve or manipulate information in storage devices and exchange information through the network cloud 115. In some examples, one or more of: the connected pill dispenser 110, wearable device 120, mobile device 130, pharmacy server 150, or payer management server 195 may include various applications implemented as processor-executable program instructions. In some embodiments, various processor-executable program instruction applications may also be used to manipulate information stored remotely and process and analyze data stored remotely across the network cloud 115 (for example, the Internet). According to an exemplary embodiment, as shown in FIG. 2, exchange of information through the network cloud 115 or other network may occur through one or more high speed connections. In some cases, high speed connections may be over-the-air (OTA), passed through networked systems, directly connected to one or more network cloud 115 or directed through one or more router. In various implementations, one or more router may be optional, and other embodiments in accordance with the present disclosure may or may not utilize one or more router. One of ordinary skill in the art would appreciate that there are numerous ways any or all of the depicted devices may connect with the network cloud 115 for the exchange of information, and embodiments of the present disclosure are contemplated for use with any method for connecting to networks for the purpose of exchanging information. Further, while this application may refer to high speed connections, embodiments of the present disclosure may be utilized with connections of any useful speed. In an illustrative example, components or modules of the system may connect to one or more of: the connected pill dispenser 110, wearable device 120, mobile device 130, pharmacy server 150, server 195, or the web portal 165 (depicted in FIG. 1, representing the doctor's office, pharmacy or the payer) via the network cloud 115 or other network in numerous ways. For instance, a component or module may connect to the system i) through a computing device directly connected to the network cloud 115, ii) through a computing device connected to the network cloud 115 through a routing device, or iii) through a computing device connected to a wireless access point. One of ordinary skill in the art will appreciate that there are numerous ways that a component or module may connect to a device via network cloud 115 or other network, and embodiments of the present disclosure are contemplated for use with any network connection method. In various examples, one or more of: the connected pill dispenser 110, wearable device 120, mobile device 130, pharmacy server 150, or payer management server 195 could include a personal computing device, such as a smartphone, tablet computer, wearable computing device, cloud-based computing device, virtual computing device, or desktop computing device, configured to operate as a host for other computing devices to connect to. In some examples, one or more communications means of the system may be any circuitry or other means for communicating data over one or more networks or to one or more peripheral devices attached to the system, or to a system module or component. Appropriate communications means may include, but are not limited to, wireless connections, wired connections, cellular connections, data port connections, Bluetooth® connections, near field communications (NFC) connections, or any combination thereof. One of ordinary skill in the art will appreciate that there are numerous communications means that may be utilized with embodiments of the present disclosure, and embodiments of the present disclosure are contemplated for use with any communications means.

Figure 3:
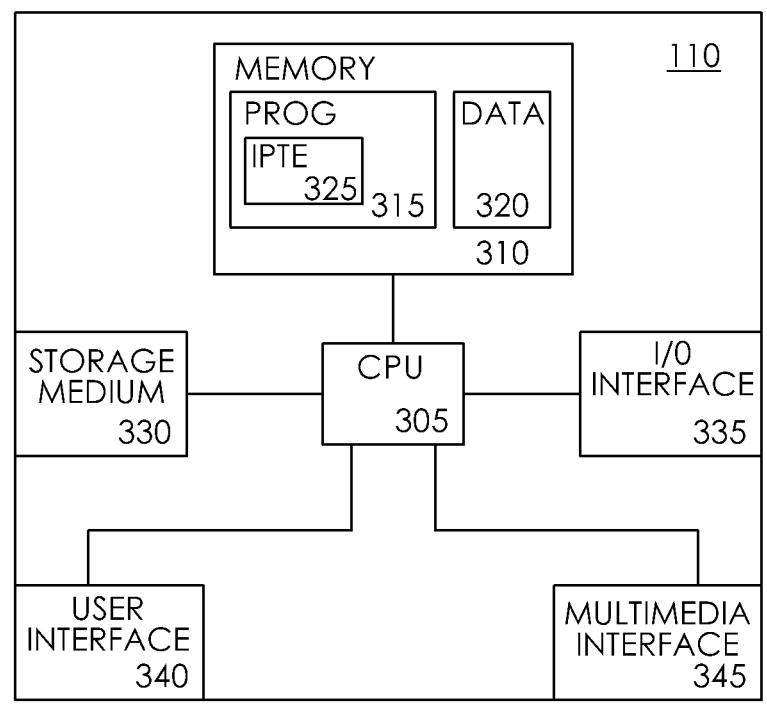
FIG. 3 depicts a structural view of an exemplary connected pill dispenser configured to improve a patient's medication adherence.

FIG. 3 depicts a structural view of an exemplary connected pill dispenser configured to improve a patient's medication adherence. In FIG. 3, the block diagram of the exemplary connected pill dispenser 110 includes processor 305 and memory 310. The processor 305 is in electrical communication with the memory 310. The depicted memory 310 includes program memory 315 and data memory 320. The depicted program memory 315 includes processor-executable program instructions implementing the IPTE (Interactive Patient Treatment Engine) 325. In some embodiments, the IPTE 325 may be upgradeable remotely via over-the-air (OTA) methods, or locally using methods such as Bluetooth connection with a mobile device or a thumb drive using USB port for manual upgrade. In some embodiments, the illustrated program memory 315 may include processor-executable program instructions configured to implement an OS (Operating System). In various embodiments, the OS may include processor executable program instructions configured to implement various operations when executed by the processor 305. In some embodiments, the OS may be omitted. In some embodiments, the illustrated program memory 315 may include processor-executable program instructions configured to implement various Application Software. In various embodiments, the application software may be upgradeable remotely via over-the-air (OTA) methods, or locally using methods such as Bluetooth connection with a mobile device or a thumb drive using USB port for manual upgrade. In various embodiments, the Application Software may include processor executable program instructions configured to implement various operations when executed by the processor 305. In some embodiments, the Application Software may be omitted. In the depicted embodiment, the processor 305 is communicatively and operably coupled with the storage medium 330. In the depicted embodiment, the processor 305 is communicatively and operably coupled with the I/O (Input/Output) interface 335. In the depicted embodiment, the I/O interface 335 includes a network interface. In various implementations, the network interface may be a wireless network interface. In some designs, the network interface may be a Wi-Fi interface. In some embodiments, the network interface may be a Bluetooth interface. In various embodiments, the network interface may include a cellular WAN (WWAN) interface. In an illustrative example, the connected pill dispenser 110 may include more than one network interface. In some designs, the network interface may be a wireline interface. In some designs, the network interface may be omitted. In the depicted embodiment, the processor 305 is communicatively and operably coupled with the user interface 340. In various implementations, the user interface 340 may be adapted to receive input from a user or send output to a user. In some embodiments, the user interface 340 may be adapted to an input-only or output-only user interface mode. In various implementations, the user interface 340 may include an imaging display. In some embodiments, the user interface 340 may include an audio interface. In some designs, the audio interface may include an audio input. In various designs, the audio interface may include an audio output. In some implementations, the user interface 340 may be touch-sensitive. In some designs, the connected pill dispenser 110 may include an accelerometer operably coupled with the processor 305. In various embodiments, the connected pill dispenser 110 may include a GPS module operably coupled with the processor 305. In an illustrative example, the connected pill dispenser 110 may include a magnetometer operably coupled with the processor 305. In some embodiments, the user interface 340 may include an input sensor array. In various implementations, the input sensor array may include one or more imaging sensor. In various designs, the input sensor array may include one or more audio transducer. In some implementations, the input sensor array may include a radio-frequency detector. In an illustrative example, the input sensor array may include an ultrasonic audio transducer. In some embodiments, the input sensor array may include image sensing subsystems or modules configurable by the processor 305 to be adapted to provide image input capability, image output capability, image sampling, spectral image analysis, correlation, autocorrelation, Fourier transforms, image buffering, image filtering operations including adjusting frequency response and attenuation characteristics of spatial domain and frequency domain filters, image recognition, pattern recognition, or anomaly detection. In various implementations, the depicted memory 310 may contain processor executable program instruction modules configurable by the processor 305 to be adapted to provide image input capability, image output capability, image sampling, spectral image analysis, correlation, autocorrelation, Fourier transforms, image buffering, image filtering operations including adjusting frequency response and attenuation characteristics of spatial domain and frequency domain filters, image recognition, pattern recognition, or anomaly detection. In some embodiments, the input sensor array may include audio sensing subsystems or modules configurable by the processor 305 to be adapted to provide audio input capability, audio output capability, audio sampling, spectral audio analysis, correlation, autocorrelation, Fourier transforms, audio buffering, audio filtering operations including adjusting frequency response and attenuation characteristics of temporal domain and frequency domain filters, audio pattern recognition, or anomaly detection. In various implementations, the depicted memory 310 may contain processor executable program instruction modules configurable by the processor 305 to be adapted to provide audio input capability, audio output capability, audio sampling, spectral audio analysis, correlation, autocorrelation, Fourier transforms, audio buffering, audio filtering operations including adjusting frequency response and attenuation characteristics of temporal domain and frequency domain filters, audio pattern recognition, or anomaly detection. In the depicted embodiment, the processor 305 is communicatively and operably coupled with the multimedia interface 345. In the illustrated embodiment, the multimedia interface 345 includes interfaces adapted to input and output of audio, video, and image data. In some embodiments, the multimedia interface 345 may include one or more still image camera or video camera. In various designs, the multimedia interface 345 may include one or more microphone. In some implementations, the multimedia interface 345 may include a wireless communication means configured to operably and communicatively couple the multimedia interface 345 with a multimedia data source or sink external to the connected pill dispenser 110. In various designs, the multimedia interface 345 may include interfaces adapted to send, receive, or process encoded audio or video. In various embodiments, the multimedia interface 345 may include one or more video, image, or audio encoder. In various designs, the multimedia interface 345 may include one or more video, image, or audio decoder. In various implementations, the multimedia interface 345 may include interfaces adapted to send, receive, or process one or more multimedia stream. In various implementations, the multimedia interface 345 may include a GPU. In some embodiments, the multimedia interface 345 may be omitted. Useful examples of the illustrated connected pill dispenser 110 include, but are not limited to, personal computers, servers, tablet PCs, smartphones, or other computing devices. In some embodiments, multiple connected pill dispenser 110 devices may be operably linked to form a computer network in a manner as to distribute and share one or more resources, such as clustered computing devices and server banks/farms. Various examples of such general-purpose multi-unit computer networks suitable for embodiments of the disclosure, their typical configuration and many standardized communication links are well known to one skilled in the art, as explained in more detail in the foregoing FIG. 2 description. In some embodiments, an exemplary connected pill dispenser 110 design may be realized in a distributed implementation. In an illustrative example, some connected pill dispenser 110 designs may be partitioned between a client device, such as, for example, a phone, and, a more powerful server system, as depicted, for example, in FIG. 2. In various designs, a connected pill dispenser 110 partition hosted on a PC or mobile device may choose to delegate some parts of computation, such as, for example, machine learning or deep learning, to a host server. In some embodiments, a client device partition may delegate computation-intensive tasks to a host server to take advantage of a more powerful processor, or to offload excess work. In an illustrative example, some devices may be configured with a mobile chip including an engine adapted to implement specialized processing, such as, for example, neural networks, machine learning, artificial intelligence, image recognition, audio processing, or digital signal processing. In some embodiments, such an engine adapted to specialized processing may have sufficient processing power to implement some features. However, in some embodiments, an exemplary connected pill dispenser 110 may be configured to operate on a device with less processing power, such as, for example, various gaming consoles, which may not have sufficient processor power, or a suitable CPU architecture, to adequately support connected pill dispenser 110. Various embodiment designs configured to operate on a such a device with reduced processor power may work in conjunction with a more powerful server system.

Figure 4:
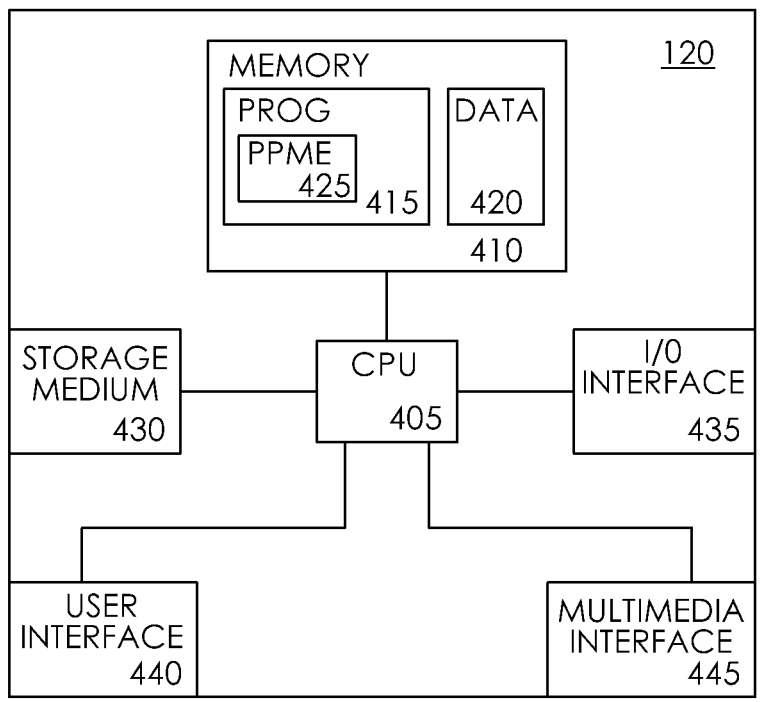
FIG. 4 depicts a structural view of an exemplary patient-wearable computing device configured to improve a patient's medication adherence.

FIG. 4 depicts a structural view of an exemplary patient-wearable computing device configured to improve a patient's medication adherence. In FIG. 4, the block diagram of the exemplary wearable device 120 includes processor 405 and memory 410. The processor 405 is in electrical communication with the memory 410. The depicted memory 410 includes program memory 415 and data memory 420. The depicted program memory 415 includes processor-executable program instructions implementing the PPME (Patient Parameter Monitoring Engine) 425. In some embodiments, the PPME 425 may be upgradeable remotely via over-the-air (OTA) methods, or locally using methods such as Bluetooth connection with a mobile device or a thumb drive using USB port for manual upgrade. In some embodiments, the illustrated program memory 415 may include processor-executable program instructions configured to implement an OS (Operating System). In various embodiments, the OS may include processor executable program instructions configured to implement various operations when executed by the processor 405. In some embodiments, the OS may be omitted. In some embodiments, the illustrated program memory 415 may include processor-executable program instructions configured to implement various Application Software. In various embodiments, the application software may be upgradeable remotely via over-the-air (OTA) methods, or locally using methods such as Bluetooth connection with a mobile device or a thumb drive using USB port for manual upgrade. In various embodiments, the Application Software may include processor executable program instructions configured to implement various operations when executed by the processor 405. In some embodiments, the Application Software may be omitted. In the depicted embodiment, the processor 405 is communicatively and operably coupled with the storage medium 430. In the depicted embodiment, the processor 405 is communicatively and operably coupled with the I/O (Input/Output) interface 435. In the depicted embodiment, the I/O interface 435 includes a network interface. In various designs, the I/O interface may include input and/or output configured to operably govern and communicate with patient parameter sensors communicatively coupled with the wearable device, such as, for example, blood pressure, blood sugar, blood oxygen level, heart rate, or body temperature. In various implementations, the network interface may be a wireless network interface.

In some designs, the network interface may be a Wi-Fi interface. In some embodiments, the network interface may be a Bluetooth interface. In various embodiments, the network interface may include a cellular WAN (WWAN) interface. In an illustrative example, the wearable device 120 may include more than one network interface. In some designs, the network interface may be a wireline interface. In some designs, the network interface may be omitted. In the depicted embodiment, the processor 405 is communicatively and operably coupled with the user interface 440. In various implementations, the user interface 440 may be adapted to receive input from a user or send output to a user. In some embodiments, the user interface 440 may be adapted to an input-only or output-only user interface mode. In various implementations, the user interface 440 may include an imaging display. In some embodiments, the user interface 440 may include an audio interface. In some designs, the audio interface may include an audio input. In various designs, the audio interface may include an audio output. In some implementations, the user interface 440 may be touch-sensitive. In some designs, the wearable device 120 may include an accelerometer operably coupled with the processor 405. In various embodiments, the wearable device 120 may include a GPS module operably coupled with the processor 405. In an illustrative example, the wearable device 120 may include a magnetometer operably coupled with the processor 405. In some embodiments, the user interface 440 may include an input sensor array. In various implementations, the input sensor array may include one or more imaging sensor. In various designs, the input sensor array may include one or more audio transducer. In some implementations, the input sensor array may include a radio-frequency detector. In an illustrative example, the input sensor array may include an ultrasonic audio transducer. In some embodiments, the input sensor array may include image sensing subsystems or modules configurable by the processor 405 to be adapted to provide image input capability, image output capability, image sampling, spectral image analysis, correlation, autocorrelation, Fourier transforms, image buffering, image filtering operations including adjusting frequency response and attenuation characteristics of spatial domain and frequency domain filters, image recognition, pattern recognition, or anomaly detection. In various implementations, the depicted memory 410 may contain processor executable program instruction modules configurable by the processor 405 to be adapted to provide image input capability, image output capability, image sampling, spectral image analysis, correlation, autocorrelation, Fourier transforms, image buffering, image filtering operations including adjusting frequency response and attenuation characteristics of spatial domain and frequency domain filters, image recognition, pattern recognition, or anomaly detection. In some embodiments, the input sensor array may include audio sensing subsystems or modules configurable by the processor 405 to be adapted to provide audio input capability, audio output capability, audio sampling, spectral audio analysis, correlation, autocorrelation, Fourier transforms, audio buffering, audio filtering operations including adjusting frequency response and attenuation characteristics of temporal domain and frequency domain filters, audio pattern recognition, or anomaly detection. In various implementations, the depicted memory 410 may contain processor executable program instruction modules configurable by the processor 405 to be adapted to provide audio input capability, audio output capability, audio sampling, spectral audio analysis, correlation, autocorrelation, Fourier transforms, audio buffering, audio filtering operations including adjusting frequency response and attenuation characteristics of temporal domain and frequency domain filters, audio pattern recognition, or anomaly detection. In the depicted embodiment, the processor 405 is communicatively and operably coupled with the multimedia interface 445. In the illustrated embodiment, the multimedia interface 445 includes interfaces adapted to input and output of audio, video, and image data. In some embodiments, the multimedia interface 445 may include one or more still image camera or video camera. In various designs, the multimedia interface 445 may include one or more microphone. In some implementations, the multimedia interface 445 may include a wireless communication means configured to operably and communicatively couple the multimedia interface 445 with a multimedia data source or sink external to the wearable device 120. In various designs, the multimedia interface 445 may include interfaces adapted to send, receive, or process encoded audio or video. In various embodiments, the multimedia interface 445 may include one or more video, image, or audio encoder. In various designs, the multimedia interface 445 may include one or more video, image, or audio decoder. In various implementations, the multimedia interface 445 may include interfaces adapted to send, receive, or process one or more multimedia stream. In various implementations, the multimedia interface 445 may include a GPU. In some embodiments, the multimedia interface 445 may be omitted. Useful examples of the illustrated wearable device 120 include, but are not limited to, personal computers, servers, tablet PCs, smartphones, or other computing devices. In some embodiments, multiple wearable device 120 devices may be operably linked to form a computer network in a manner as to distribute and share one or more resources, such as clustered computing devices and server banks/farms. Various examples of such general-purpose multi-unit computer networks suitable for embodiments of the disclosure, their typical configuration and many standardized communication links are well known to one skilled in the art, as explained in more detail in the foregoing FIG. 2 description. In some embodiments, an exemplary wearable device 120 design may be realized in a distributed implementation. In an illustrative example, some wearable device 120 designs may be partitioned between a client device, such as, for example, a phone, and, a more powerful server system, as depicted, for example, in FIG. 2. In various designs, a wearable device 120 partition hosted on a PC or mobile device may choose to delegate some parts of computation, such as, for example, machine learning or deep learning, to a host server. In some embodiments, a client device partition may delegate computation-intensive tasks to a host server to take advantage of a more powerful processor, or to offload excess work. In an illustrative example, some devices may be configured with a mobile chip including an engine adapted to implement specialized processing, such as, for example, neural networks, machine learning, artificial intelligence, image recognition, audio processing, or digital signal processing. In some embodiments, such an engine adapted to specialized processing may have sufficient processing power to implement some features. However, in some embodiments, an exemplary wearable device 120 may be configured to operate on a device with less processing power, such as, for example, various gaming consoles, which may not have sufficient processor power, or a suitable CPU architecture, to adequately support wearable device 120. Various embodiment designs configured to operate on a such a device with reduced processor power may work in conjunction with a more powerful server system.

Figure 5:
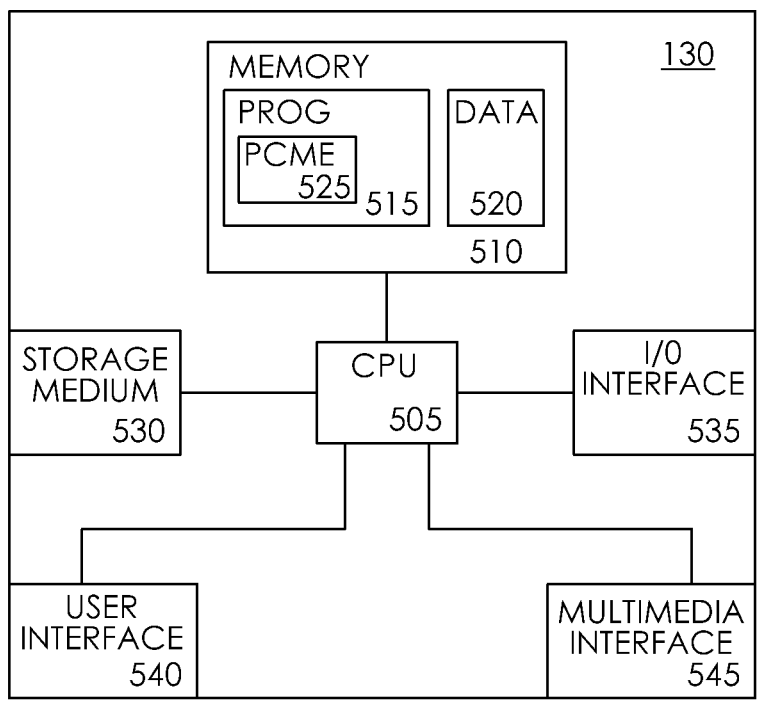
FIG. 5 depicts a structural view of an exemplary physician's mobile computing device configured to improve a patient's medication adherence.

FIG. 5 depicts a structural view of an exemplary physician's mobile computing device configured to improve a patient's medication adherence. In various examples, the exemplary mobile computing device 130 depicted by FIG. 5 may be representative of a mobile device used by a patient, pharmacy, or non-physician caregiver, as well as by a physician. In FIG. 5, the block diagram of the exemplary mobile device 130 includes processor 505 and memory 510. The processor 505 is in electrical communication with the memory 510. The depicted memory 510 includes program memory 515 and data memory 520. The depicted program memory 515 includes processor-executable program instructions implementing the PCME (Patient Care Management Engine) 525. In some embodiments, the PCME 525 may be upgradeable remotely via over-the-air (OTA) methods, or locally using methods such as Bluetooth connection with a mobile device or a thumb drive using USB port for manual upgrade. In some embodiments, the illustrated program memory 515 may include processor-executable program instructions configured to implement an OS (Operating System). In various embodiments, the OS may include processor executable program instructions configured to implement various operations when executed by the processor 505. In some embodiments, the OS may be omitted. In some embodiments, the illustrated program memory 515 may include processor-executable program instructions configured to implement various Application Software. In various embodiments, the application software may be upgradeable remotely via over-the-air (OTA) methods, or locally using methods such as Bluetooth connection with a mobile device or a thumb drive using USB port for manual upgrade. In various embodiments, the Application Software may include processor executable program instructions configured to implement various operations when executed by the processor 505. In some embodiments, the Application Software may be omitted. In the depicted embodiment, the processor 505 is communicatively and operably coupled with the storage medium 530. In the depicted embodiment, the processor 505 is communicatively and operably coupled with the I/O (Input/Output) interface 535. In the depicted embodiment, the I/O interface 535 includes a network interface. In various implementations, the network interface may be a wireless network interface. In some designs, the network interface may be a Wi-Fi interface. In some embodiments, the network interface may be a Bluetooth interface which could be utilized to connect to the connected pill dispenser 110 to perform various operations. In various embodiments, the network interface may include a cellular WAN (WWAN) interface. In an illustrative example, the mobile device 130 may include more than one network interface. In some designs, the network interface may be a wireline interface. In some designs, the network interface may be omitted. In the depicted embodiment, the processor 505 is communicatively and operably coupled with the user interface 540. In various implementations, the user interface 540 may be adapted to receive input from a user or send output to a user. In some embodiments, the user interface 540 may be adapted to an input-only or output-only user interface mode. In various implementations, the user interface 540 may include an imaging display. In some embodiments, the user interface 540 may include an audio interface. In some designs, the audio interface may include an audio input. In various designs, the audio interface may include an audio output. In some implementations, the user interface 540 may be touch-sensitive. In some designs, the mobile device 130 may include an accelerometer operably coupled with the processor 505. In various embodiments, the mobile device 130 may include a GPS module operably coupled with the processor 505. In an illustrative example, the mobile device 130 may include a magnetometer operably coupled with the processor 505. In some embodiments, the user interface 540 may include an input sensor array. In various implementations, the input sensor array may include one or more imaging sensor. In various designs, the input sensor array may include one or more audio transducer. In some implementations, the input sensor array may include a radio-frequency detector. In an illustrative example, the input sensor array may include an ultrasonic audio transducer. In some embodiments, the input sensor array may include image sensing subsystems or modules configurable by the processor 505 to be adapted to provide image input capability, image output capability, image sampling, spectral image analysis, correlation, autocorrelation, Fourier transforms, image buffering, image filtering operations including adjusting frequency response and attenuation characteristics of spatial domain and frequency domain filters, image recognition, pattern recognition, or anomaly detection. In various implementations, the depicted memory 510 may contain processor executable program instruction modules configurable by the processor 505 to be adapted to provide image input capability, image output capability, image sampling, spectral image analysis, correlation, autocorrelation, Fourier transforms, image buffering, image filtering operations including adjusting frequency response and attenuation characteristics of spatial domain and frequency domain filters, image recognition, pattern recognition, or anomaly detection. In some embodiments, the input sensor array may include audio sensing subsystems or modules configurable by the processor 505 to be adapted to provide audio input capability, audio output capability, audio sampling, spectral audio analysis, correlation, autocorrelation, Fourier transforms, audio buffering, audio filtering operations including adjusting frequency response and attenuation characteristics of temporal domain and frequency domain filters, audio pattern recognition, or anomaly detection. In various implementations, the depicted memory 510 may contain processor executable program instruction modules configurable by the processor 505 to be adapted to provide audio input capability, audio output capability, audio sampling, spectral audio analysis, correlation, autocorrelation, Fourier transforms, audio buffering, audio filtering operations including adjusting frequency response and attenuation characteristics of temporal domain and frequency domain filters, audio pattern recognition, or anomaly detection. In the depicted embodiment, the processor 505 is communicatively and operably coupled with the multimedia interface 545. In the illustrated embodiment, the multimedia interface 545 includes interfaces adapted to input and output of audio, video, and image data. In some embodiments, the multimedia interface 545 may include one or more still image camera or video camera. In various designs, the multimedia interface 545 may include one or more microphone. In some implementations, the multimedia interface 545 may include a wireless communication means configured to operably and communicatively couple the multimedia interface 545 with a multimedia data source or sink external to the mobile device 130. In various designs, the multimedia interface 545 may include interfaces adapted to send, receive, or process encoded audio or video. In various embodiments, the multimedia interface 545 may include one or more video, image, or audio encoder. In various designs, the multimedia interface 545 may include one or more video, image, or audio decoder. In various implementations, the multimedia interface 545 may include interfaces adapted to send, receive, or process one or more multimedia stream. In various implementations, the multimedia interface 545 may include a GPU. In some embodiments, the multimedia interface 545 may be omitted. Useful examples of the illustrated mobile device 130 include, but are not limited to, personal computers, servers, tablet PCs, smartphones, or other computing devices. In some embodiments, multiple mobile device 130 devices may be operably linked to form a computer network in a manner as to distribute and share one or more resources, such as clustered computing devices and server banks/farms. Various examples of such general-purpose multi-unit computer networks suitable for embodiments of the disclosure, their typical configuration and many standardized communication links are well known to one skilled in the art, as explained in more detail in the foregoing FIG. 2 description. In some embodiments, an exemplary mobile device 130 design may be realized in a distributed implementation. In an illustrative example, some mobile device 130 designs may be partitioned between a client device, such as, for example, a phone, and, a more powerful server system, as depicted, for example, in FIG. 2. In various designs, a mobile device 130 partition hosted on a PC or mobile device may choose to delegate some parts of computation, such as, for example, machine learning or deep learning, to a host server. In some embodiments, a client device partition may delegate computation-intensive tasks to a host server to take advantage of a more powerful processor, or to offload excess work. In an illustrative example, some devices may be configured with a mobile chip including an engine adapted to implement specialized processing, such as, for example, neural networks, machine learning, artificial intelligence, image recognition, audio processing, or digital signal processing. In some embodiments, such an engine adapted to specialized processing may have sufficient processing power to implement some features. However, in some embodiments, an exemplary mobile device 130 may be configured to operate on a device with less processing power, such as, for example, various gaming consoles, which may not have sufficient processor power, or a suitable CPU architecture, to adequately support mobile device 130. Various embodiment designs configured to operate on a such a device with reduced processor power may work in conjunction with a more powerful server system.

Figure 6:
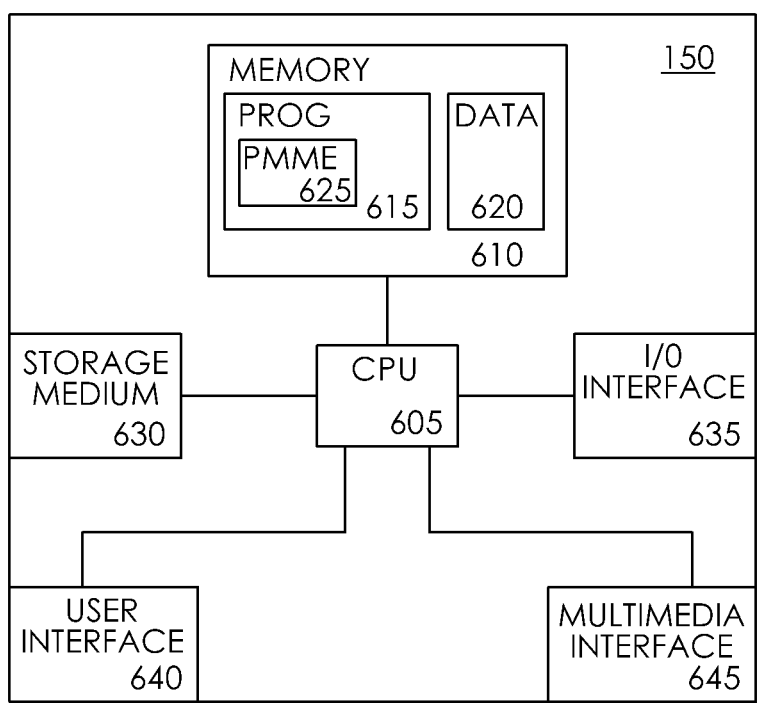
FIG. 6 depicts a structural view of an exemplary pharmacy computing device configured to improve a patient's medication adherence.

FIG. 6 depicts a structural view of an exemplary pharmacy computing device configured to improve a patient's medication adherence. In some examples, the exemplary pharmacy server 150 depicted by FIG. 6 may be representative of a computing device used by a doctor's office, or a payer, as well as by a pharmacy. In FIG. 6, the block diagram of the exemplary pharmacy server 150 includes processor 605 and memory 610. The processor 605 is in electrical communication with the memory 610. The depicted memory 610 includes program memory 615 and data memory 620. The depicted program memory 615 includes processor-executable program instructions implementing the PMME (Prescription Medication Management Engine) 625. In some embodiments, the PMME 625 may be upgradeable remotely via over-the-air (OTA) methods, or locally using methods such as Bluetooth connection with a mobile device or a thumb drive using USB port for manual upgrade. In various implementations, the processor-executable program instructions implementing the PMME 625 may be fetched from a central server or web portal. In some embodiments, the illustrated program memory 615 may include processor-executable program instructions configured to implement an OS (Operating System). In various embodiments, the OS may include processor executable program instructions configured to implement various operations when executed by the processor 605. In some embodiments, the OS may be omitted. In some embodiments, the illustrated program memory 615 may include processor-executable program instructions configured to implement various Application Software. In various embodiments, the application software may be upgradeable remotely via over-the-air (OTA) methods, or locally using methods such as Bluetooth connection with a mobile device or a thumb drive using USB port for manual upgrade. In various embodiments, the Application Software may include processor executable program instructions configured to implement various operations when executed by the processor 605. In some embodiments, the Application Software may be omitted. In the depicted embodiment, the processor 605 is communicatively and operably coupled with the storage medium 630. In the depicted embodiment, the processor 605 is communicatively and operably coupled with the I/O (Input/Output) interface 635. In the depicted embodiment, the I/O interface 635 includes a network interface. In various implementations, the network interface may be a wireless network interface. In some designs, the network interface may be a Wi-Fi interface. In some embodiments, the network interface may be a Bluetooth interface. In various embodiments, the network interface may include a cellular WAN (WWAN) interface. In an illustrative example, the pharmacy server 150 may include more than one network interface. In some designs, the network interface may be a wireline interface. In some designs, the network interface may be omitted. In the depicted embodiment, the processor 605 is communicatively and operably coupled with the user interface 640. In various implementations, the user interface 640 may be adapted to receive input from a user or send output to a user. In some embodiments, the user interface 640 may be adapted to an input-only or output-only user interface mode. In various implementations, the user interface 640 may include an imaging display. In some embodiments, the user interface 640 may include an audio interface. In some designs, the audio interface may include an audio input. In various designs, the audio interface may include an audio output. In some implementations, the user interface 640 may be touch-sensitive. In some designs, the pharmacy server 150 may include an accelerometer operably coupled with the processor 605. In various embodiments, the pharmacy server 150 may include a GPS module operably coupled with the processor 605. In an illustrative example, the pharmacy server 150 may include a magnetometer operably coupled with the processor 605. In some embodiments, the user interface 640 may include an input sensor array. In various implementations, the input sensor array may include one or more imaging sensor. In various designs, the input sensor array may include one or more audio transducer. In some implementations, the input sensor array may include a radio-frequency detector. In an illustrative example, the input sensor array may include an ultrasonic audio transducer. In some embodiments, the input sensor array may include image sensing subsystems or modules configurable by the processor 605 to be adapted to provide image input capability, image output capability, image sampling, spectral image analysis, correlation, autocorrelation, Fourier transforms, image buffering, image filtering operations including adjusting frequency response and attenuation characteristics of spatial domain and frequency domain filters, image recognition, pattern recognition, or anomaly detection. In various implementations, the depicted memory 610 may contain processor executable program instruction modules configurable by the processor 605 to be adapted to provide image input capability, image output capability, image sampling, spectral image analysis, correlation, autocorrelation, Fourier transforms, image buffering, image filtering operations including adjusting frequency response and attenuation characteristics of spatial domain and frequency domain filters, image recognition, pattern recognition, or anomaly detection. In some embodiments, the input sensor array may include audio sensing subsystems or modules configurable by the processor 605 to be adapted to provide audio input capability, audio output capability, audio sampling, spectral audio analysis, correlation, autocorrelation, Fourier transforms, audio buffering, audio filtering operations including adjusting frequency response and attenuation characteristics of temporal domain and frequency domain filters, audio pattern recognition, or anomaly detection. In various implementations, the depicted memory 610 may contain processor executable program instruction modules configurable by the processor 605 to be adapted to provide audio input capability, audio output capability, audio sampling, spectral audio analysis, correlation, autocorrelation, Fourier transforms, audio buffering, audio filtering operations including adjusting frequency response and attenuation characteristics of temporal domain and frequency domain filters, audio pattern recognition, or anomaly detection. In the depicted embodiment, the processor 605 is communicatively and operably coupled with the multimedia interface 645. In the illustrated embodiment, the multimedia interface 645 includes interfaces adapted to input and output of audio, video, and image data. In some embodiments, the multimedia interface 645 may include one or more still image camera or video camera. In various designs, the multimedia interface 645 may include one or more microphone. In some implementations, the multimedia interface 645 may include a wireless communication means configured to operably and communicatively couple the multimedia interface 645 with a multimedia data source or sink external to the pharmacy server 150. In various designs, the multimedia interface 645 may include interfaces adapted to send, receive, or process encoded audio or video. In various embodiments, the multimedia interface 645 may include one or more video, image, or audio encoder. In various designs, the multimedia interface 645 may include one or more video, image, or audio decoder. In various implementations, the multimedia interface 645 may include interfaces adapted to send, receive, or process one or more multimedia stream. In various implementations, the multimedia interface 645 may include a GPU. In some embodiments, the multimedia interface 645 may be omitted. Useful examples of the illustrated pharmacy server 150 include, but are not limited to, personal computers, servers, tablet PCs, smartphones, or other computing devices. In some embodiments, multiple pharmacy server 150 devices may be operably linked to form a computer network in a manner as to distribute and share one or more resources, such as clustered computing devices and server banks/farms. Various examples of such general-purpose multi-unit computer networks suitable for embodiments of the disclosure, their typical configuration and many standardized communication links are well known to one skilled in the art, as explained in more detail in the foregoing FIG. 2 description. In some embodiments, an exemplary pharmacy server 150 design may be realized in a distributed implementation. In an illustrative example, some pharmacy server 150 designs may be partitioned between a client device, such as, for example, a phone, and, a more powerful server system, as depicted, for example, in FIG. 2. In various designs, a pharmacy server 150 partition hosted on a PC or mobile device may choose to delegate some parts of computation, such as, for example, machine learning or deep learning, to a host server. In some embodiments, a client device partition may delegate computation-intensive tasks to a host server to take advantage of a more powerful processor, or to offload excess work. In an illustrative example, some devices may be configured with a mobile chip including an engine adapted to implement specialized processing, such as, for example, neural networks, machine learning, artificial intelligence, image recognition, audio processing, or digital signal processing. In some embodiments, such an engine adapted to specialized processing may have sufficient processing power to implement some features. However, in some embodiments, an exemplary pharmacy server 150 may be configured to operate on a device with less processing power, such as, for example, various gaming consoles, which may not have sufficient processor power, or a suitable CPU architecture, to adequately support pharmacy server 150. Various embodiment designs configured to operate on a such a device with reduced processor power may work in conjunction with a more powerful server system.

Figure 7:
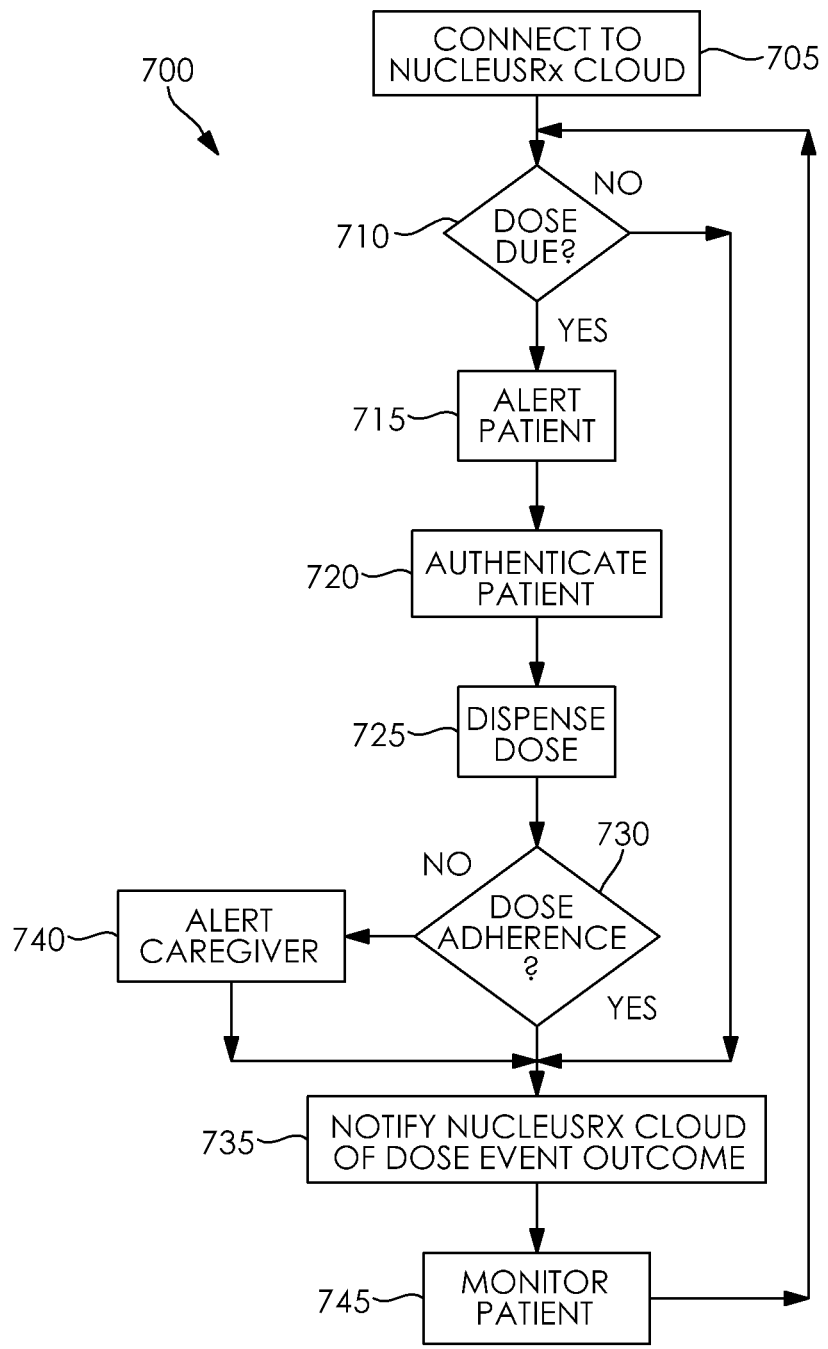
FIG. 7 depicts an exemplary process flow of an embodiment Interactive Patient Treatment Engine (IPTE) improving a patient's medication adherence.

FIG. 7 depicts an exemplary process flow of an embodiment Interactive Patient Treatment Engine (IPTE) improving a patient's medication adherence. The method depicted in FIG. 7 is given from the perspective of the IPTE 325 implemented via processor-executable program instructions executing on the connected pill dispenser 110 processor 305, depicted in FIG. 3. In the illustrated embodiment, the IPTE 325 executes as program instructions on the processor 305 configured in the IPTE 325 host connected pill dispenser 110, depicted in at least FIG. 1, FIG. 2, and FIG. 3. In some embodiments, the IPTE 325 may execute as a cloud service communicatively and operatively coupled with system services, hardware resources, or software elements local to and/or external to the IPTE 325 host connected pill dispenser 110. The depicted method 700 begins at step 705 with the processor 305 connecting to the NucleusRx cloud. Then, the method continues at step 710 with the processor 305 performing a test to determine if a dose is due. Upon a determination by the processor 305 at step 710 that a dose is not due, the method continues at step 735 with the processor 305 notifying the NucleusRx cloud that a dose was not delivered because a dose was not due, and the method continues at step 745 with the processor 305 monitoring the patient. Upon a determination by the processor 305 at step 710 that a dose is due, the method continues at step 715 with the processor 305 alerting the patient that a dose is due. The method continues at step 720 with the processor 305 authenticating the patient. Then, the method continues at step 725 with the processor 305 dispensing the dose. The method continues at step 730 with the processor 305 determining dose adherence, including determining based on sensor input if the patient consumed the dose. Upon a determination by the processor 305 at step 730 the patient did not consume the dose, the method continues at step 740 with the processor 305 alerting the caregiver to the missed dose, and the method continues at step 735 with the processor 305 notifying the Nucleus Rx cloud of the dose event outcome. Upon a determination by the processor 305 at step 730 the patient did consume the dose, the method continues at step 735 with the processor 305 notifying the NucleusRx cloud of the dose event outcome. For example, at step 735 the processor 305 may notify the NucleusRx cloud of a dose event outcome including: dose missed, dose dispensed, erroneous dispense, or dispense failed. Then, the method continues at step 745 with the processor 305 monitoring the patient, and the method continues at step 710 with the processor 305 performing a test to determine if a dose is due.

Figure 8:
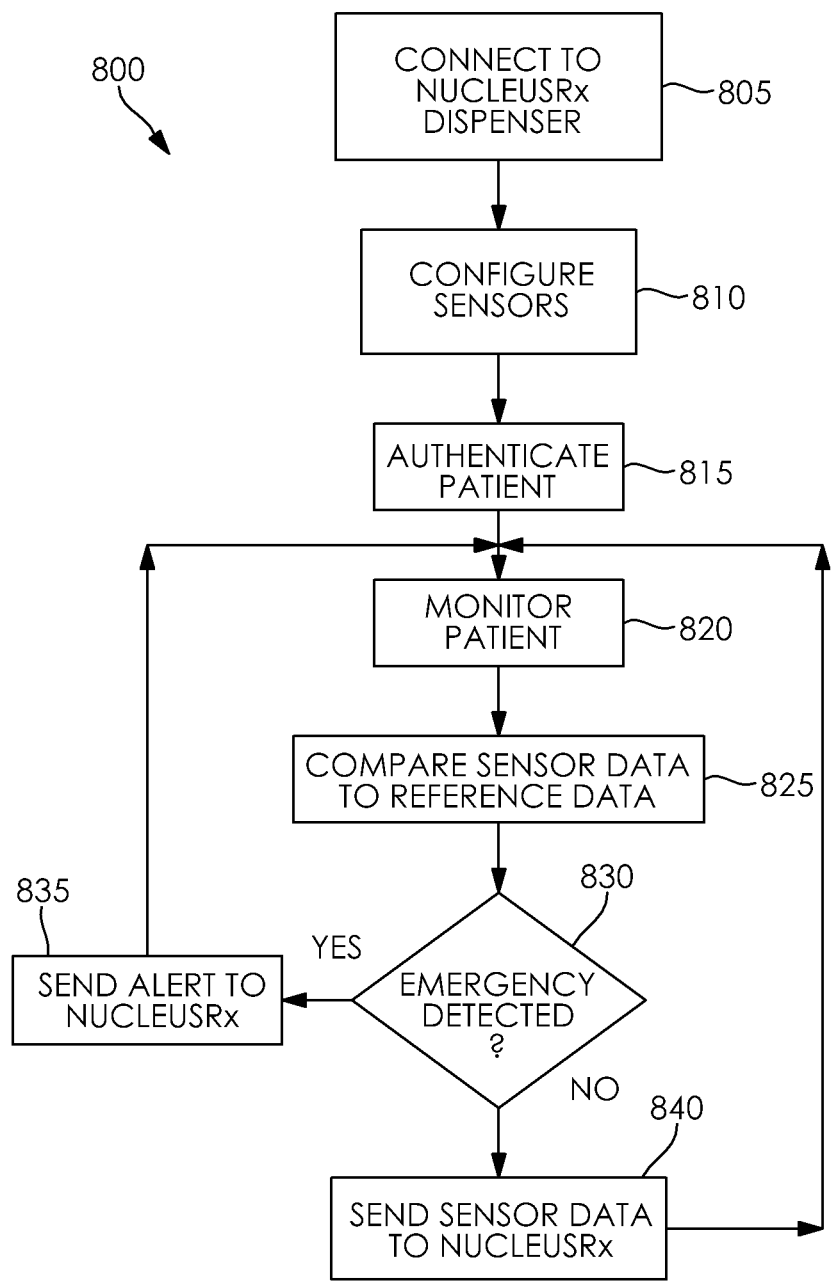
FIG. 8 depicts an exemplary process flow of an embodiment Patient Parameter Monitoring Engine (PPME) improving a patient's medication adherence.

FIG. 8 depicts an exemplary process flow of an embodiment Patient Parameter Monitoring Engine (PPME) improving a patient's medication adherence. The method depicted in FIG. 8 is given from the perspective of the PPME 425 implemented via processor-executable program instructions executing on the wearable device 120 processor 405, depicted in FIG. 4. In the illustrated embodiment, the PPME 425 executes as program instructions on the processor 405 configured in the PPME 425 host wearable device 120, depicted in at least FIG. 1, FIG. 2, and FIG. 4. In some embodiments, the PPME 425 may execute as a cloud service communicatively and operatively coupled with system services, hardware resources, or software elements local to and/or external to the PPME 425 host wearable device 120. The depicted method 800 begins at step 805 with the processor 405 connecting to the NucleusRx dispenser. In addition to connecting with the dispenser, the wearable device could be connected to the pharmacy or the authorized caregiver's mobile app for configuration. In an illustrative example, configuration parameters can be pushed by the doctor's office or the pharmacist via the dispensers to the patient's wearable device. In some examples, similar configuration may be achieved by pharmacist's mobile app during a face-to-face set up, or similarly with the authorized caregiver's mobile app. In various embodiments, the connection to the dispenser will also be required for external patient authentication (for example, using touch ID of the wearable) for dispensing meds. In some scenarios, for the purpose of configuration of patient parameters, the wearable could be connected to the central server. Then, the method continues at step 810 with the processor 405 configuring patient monitoring sensors. Then the method continues at step 815 with the processor 405 authenticating the patient based on sensor input. Then, the method continues at step 820 with the processor 405 monitoring the patient based on the sensor data, and the method continues at step 825 with the processor 405 comparing the sensor data to reference sensor data representative of patient baseline condition. At step 830, the processor 405 performs a test to determine if a patient emergency condition is detected by the processor 405, based on the comparison performed by the processor 405 at step 825. Upon a determination by the processor 405 at step 830 that a patient emergency condition is detected, the method continues at step 835 with the processor 405 sending an alert representative of the emergency condition to NucleusRx, and the method continues at step 820 with the processor 405 monitoring the patient. Upon a determination by the processor 405 at step 830 that a patient emergency condition is not detected, the method continues at step 840 with the processor 840 sending the patient monitor sensor data to NucleusRx, and the method continues at step 820 with the processor 405 monitoring the patient.

Figure 9:
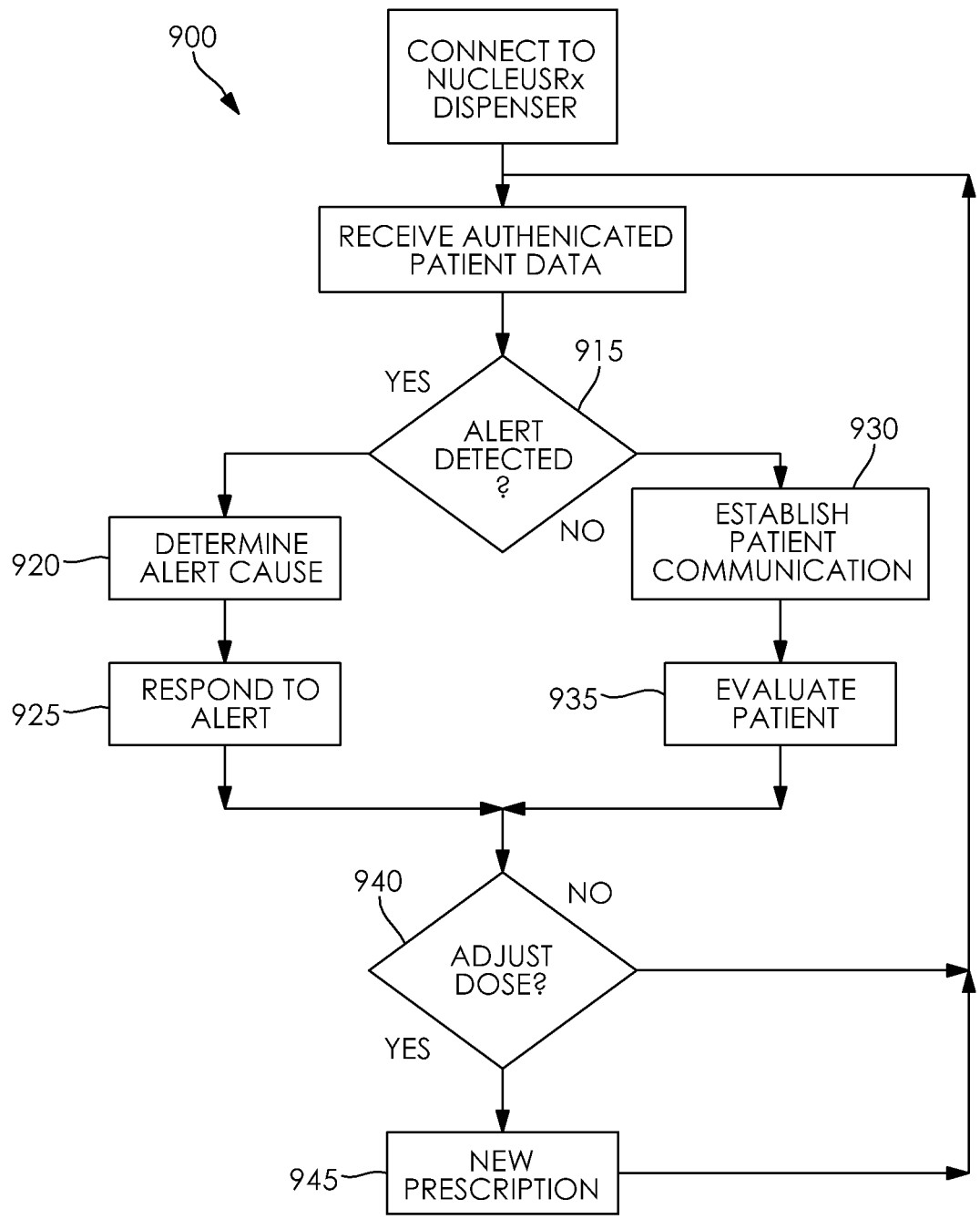
FIG. 9 depicts an exemplary process flow of an embodiment Patient Care Management Engine (PCME) improving a patient's medication adherence.

FIG. 9 depicts an exemplary process flow of an embodiment Patient Care Management Engine (PCME) improving a patient's medication adherence. The method depicted in FIG. 9 is given from the perspective of the PCME 525 implemented via processor-executable program instructions executing on the mobile device 130 processor 505, depicted in FIG. 5. In various embodiment implementations, the scope of PCME 525 target computing platforms may include collaborative computing distributed across multiple cloud and device-centric processors. In an illustrative example, the main computation may take place on NucleusRX's central server or the cloud platform. The central server or the cloud platform may collect data from the dispenser and the wearable, and compute against the prescription configured by the pharmacy and the patient parameters set by the doctor's office. The platform may then disseminate action and information to the subscribed parties—doctor's mobile device and/or web portal, pharmacist's mobile device and/or web portal, caregiver's mobile device. In some designs, the prescription configuration by the pharmacists, and the patient parameters set by the doctor's office, may be mutually exclusive activities. Prescription information and pill count may alert the pharmacy about replenishment requirements, whereas, patient's parameters may allow a doctor to adjust medication, which may in-turn adjust the medication replenishments needs for the pharmacy. In the illustrated embodiment, the PCME 525 executes as program instructions on the processor 505 configured in the PCME 525 host mobile device 130, depicted in at least FIG. 1, FIG. 2, and FIG. 5. In some embodiments, the PCME 525 may execute as a cloud service communicatively and operatively coupled with system services, hardware resources, or software elements local to and/or external to the PCME 525 host mobile device 130. The depicted method 900 begins at step 905 with the processor 505 connecting to the NucleusRx dispenser. Then, the method continues at step 910 with the processor 505 receiving authenticated patient data. The method continues at step 915 with the processor 505 performing a test to determine if an alert is detected. Upon a determination by the processor 505 at step 915 an alert was detected, the method continues with the processor 505 at step 920 determining the alert cause, and the processor 505 at step 925 responding to the alert. Upon a determination by the processor 505 at step 915 an alert was not detected, the method continues with the processor 505 at step 930 establishing patient communication, and the processor 505 at step 935 evaluating the patient. Then, the method continues at step 940 with the processor 505 performing a test to determine if the patient's dose should be adjusted, in response to either the alert or evaluation. Upon a determination by the processor 505 at step 940 the dose should be adjusted, the method continues a step 945 with the processor 505 generating a new prescription based on a prescribed treatment protocol, and the method continues at step 910 with the processor 505 receiving authenticated patient data.

Figure 10:
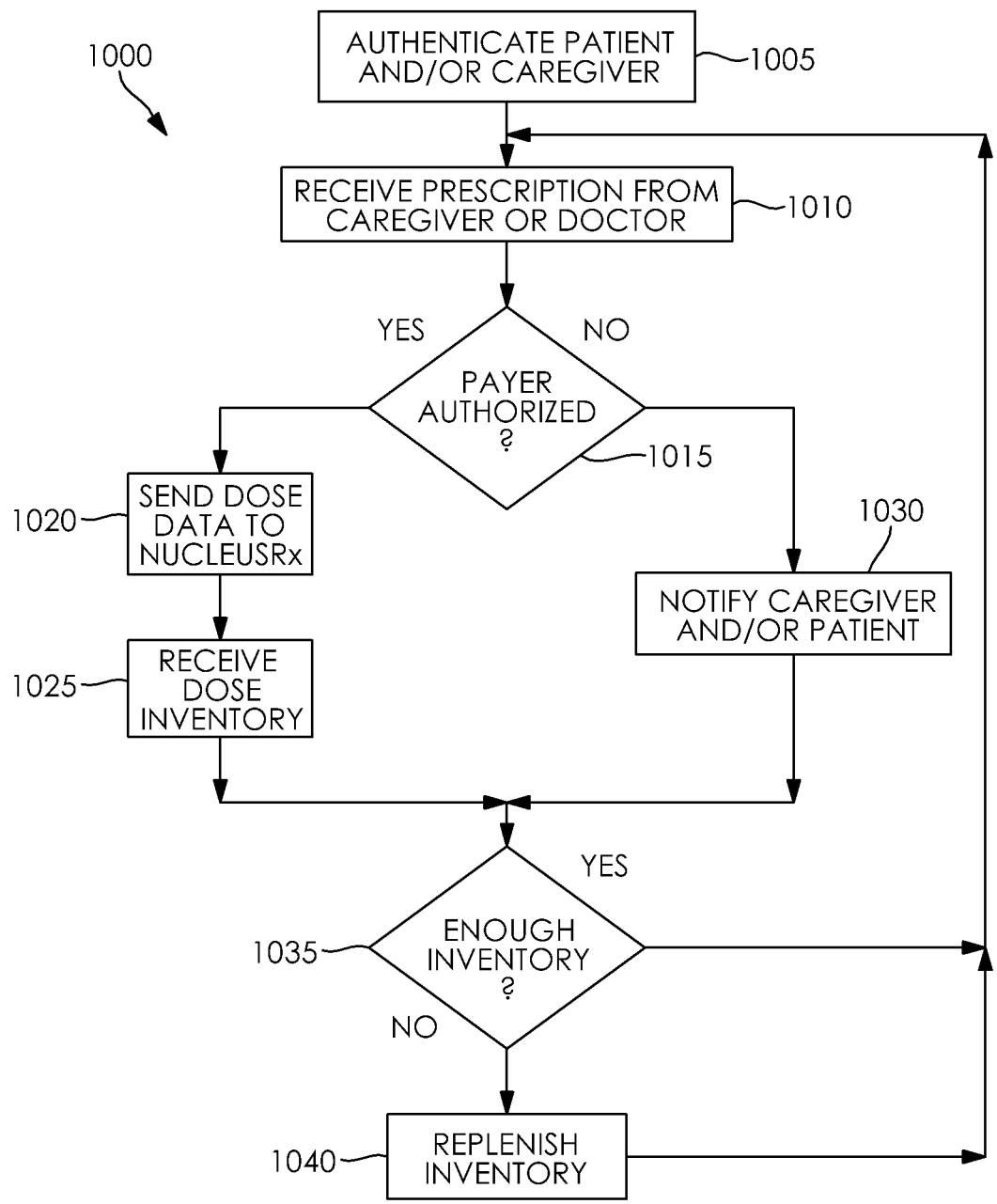
FIG. 10 depicts an exemplary process flow of an embodiment Prescription Medication Management Engine (PMME) improving a patient's medication adherence.

FIG. 10 depicts an exemplary process flow of an embodiment Prescription Medication Management Engine (PMME) improving a patient's medication adherence. The method depicted in FIG. 10 is given from the perspective of the PMME 625 implemented via processor-executable program instructions executing on the pharmacy server 150 processor 605, depicted in FIG. 6. In the depicted example, the pharmacy manages through a web portal or a mobile app, and the information exchange is through the central cloud server. In the illustrated embodiment, the PMME 625 executes as program instructions on the processor 605 configured in the PMME 625 host pharmacy server 150, depicted in at least FIG. 1, FIG. 2, and FIG. 6. In some embodiments, the PMME 625 may execute as a cloud service communicatively and operatively coupled with system services, hardware resources, or software elements local to and/or external to the PMME 625 host pharmacy server 150. The depicted method 1000 begins at step 1005 with the processor 605 authenticating the patient and/or caregiver. Then, the method continues at step 1010 with the processor 605 receiving a new prescription from the caregiver or doctor. In some embodiments, the treatment regime using the connected pill dispenser is recommended by the doctor and the payer pays for the treatment. In this case, the doctor writes the new prescription including the connected pill dispenser. The prescription may come directly from the doctor to the pharmacy system, or the patient/caregiver may manually provide the prescription to the pharmacy. In various implementations, when the device is paid for by the provider (for example, a hospital, or a healthcare facility), the caregiver/patient will provide the prescription. At step 1015, the processor 605 performs a test to determine if the prescription received from the caregiver is authorized by a payer. Upon a determination by the processor 605 at step 1015 the prescription is authorized, the method continues with the processor 605 at step 1020 sending dose data to the NucleusRx dispenser, and the processor receiving at step 1025 dose inventory data from the NucleusRx dispenser. Upon a determination by the processor 605 at step 1015 the prescription is not authorized, the processor 605 at step 1030 notifies the caregiver and/or patient the prescription is not payer authorized. The method continues at step 1035 with the processor 605 performing a test to determine if the NucleusRx dispenser has sufficient medication dose inventory. Upon a determination by the processor 605 at step 1035 the NucleusRx dispenser does not have sufficient medication dose inventory, the method continues at step 1040 with the processor 605 replenishing the NucleusRx dispenser medication dose inventory. Then, the method continues at step 1010 with the processor 605 receiving a prescription from the caregiver or doctor.

Figure 11:
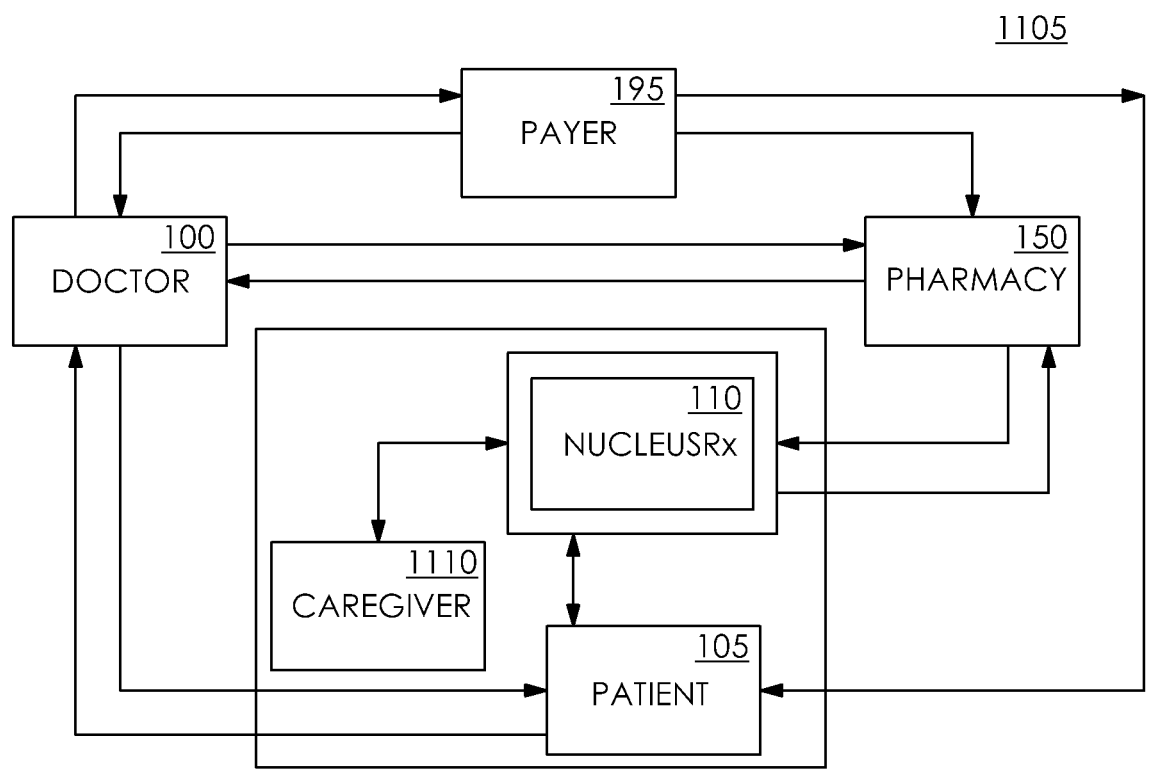
FIG. 11 depicts an exemplary collaboration diagram illustrating patient, provider, payer, and caregiver interaction to enhance a patient's medication adherence.

FIG. 11 depicts an exemplary collaboration diagram illustrating patient, provider, payer, and caregiver interaction to enhance a patient's medication adherence. In FIG. 11, the doctor 100 prescribes medication to treat the patient 105 with the assistance of the NucleusRx connected pill dispenser 110. In the depicted example, the NucleusRx connected pill dispenser 110 gets medications for the patient 105, and sends alerts when doses are missed. In various embodiments, the NucleusRx connected pill dispenser 110 may send a missed dose alert to one or more caregiver 1110. In some embodiments, the NucleusRx connected pill dispenser 110 may send a missed dose alert to the patient 105 or to the doctor 100. Various NucleusRx connected pill dispenser 110 designs may notify the caregiver 1110 or doctor 100 of medication adherence or medication compliance determined by the NucleusRx connected pill dispenser 110 as a function of sensor data. In various embodiments, medication adherence or medication compliance may be determined by the NucleusRx connected pill dispenser 110 as a function of data captured by one or more sensor configured in a patient-controlled device, a patient wearable device, or the NucleusRx connected pill dispenser 110. In the illustrated embodiment, the NucleusRx connected pill dispenser 110 sends patient 105 vital and parametric information collected from one or more wearable device to the doctor 100. In the depicted example, the doctor 100 prescribes a modified patient 105 medication dose adjusted as a function of the patient 105 vital and parametric information received from the NucleusRx connected pill dispenser 110. In the illustrated embodiment, the doctor 100 sends the modified patient 105 medication dose to the NucleusRx connected pill dispenser 110. In the depicted example, the caregiver 1110 may also receive medications from the NucleusRx connected pill dispenser 110, receive alerts from the NucleusRx connected pill dispenser 110 on a missed dose, or receive notification of compliance from the NucleusRx connected pill dispenser 110. In various embodiments, the doctor 100 may diagnose the patient 105 medical condition based on an evaluation of the patient 105 medical history. In some examples, the doctor 100 may determine treatment of the patient 105 medical condition using the NucleusRx connected pill dispenser 110 is medically indicated, based on the patient 105 medical condition diagnosed by the doctor 100. In the depicted embodiment, the doctor 100 prescribes the NucleusRx connected pill dispenser 110 based on the patient 105 medical condition. In the illustrated example, the doctor 100 forwards scripts or a change of scripts to the pharmacy 150. In the illustrated example, the pharmacy 150 forwards manual patient 105 compliance reports to the doctor 100. In the depicted example, the NucleusRx connected pill dispenser 110 alerts the pharmacy 150 for refills. In the illustrated example, the NucleusRx connected pill dispenser 110 notifies the pharmacy 150 of compliance. In the depicted example, the pharmacy 150 fills the prescriptions, programs medication schedules into the NucleusRx connected pill dispenser 110, and trains both patients and caregivers. In the illustrated example, the payer 195 authorizes the patient 105 treatment using the NucleusRx connected pill dispenser 110, and the payer 195 pays the doctor 100 for services. In the depicted example, the payer 195 pays the pharmacy 150 for medications, the use of the NucleusRx connected pill dispenser 110, and the pharmacy 150 dispensing services.

Figure 12:
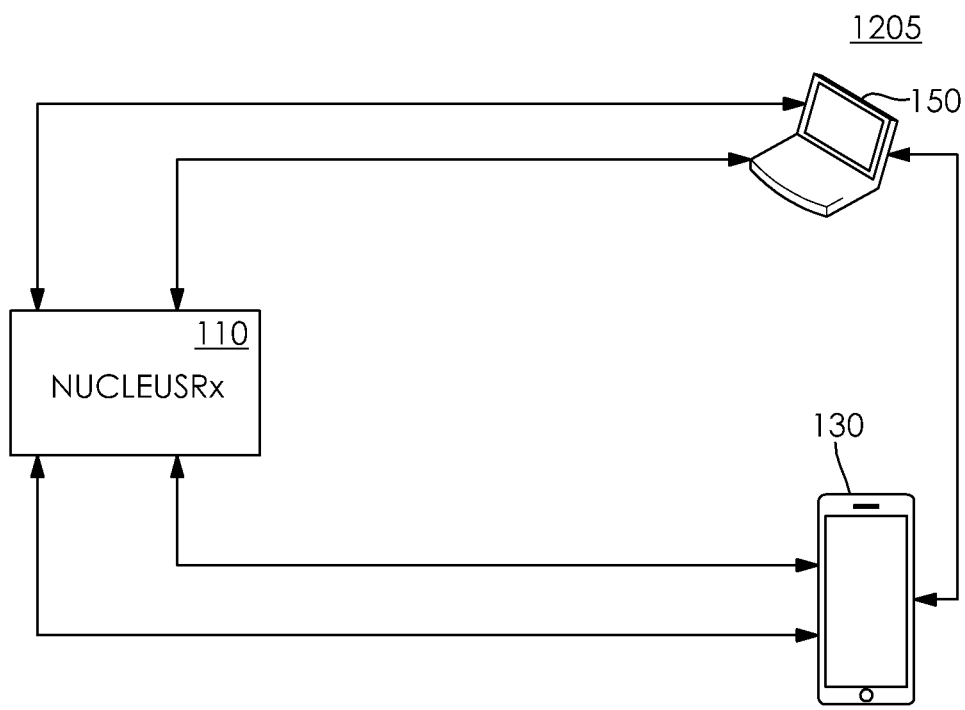
FIG. 12 depicts an exemplary conceptual diagram illustrating NucleusRx components and interactions to enhance a patient's medication adherence.
Figure 13A:
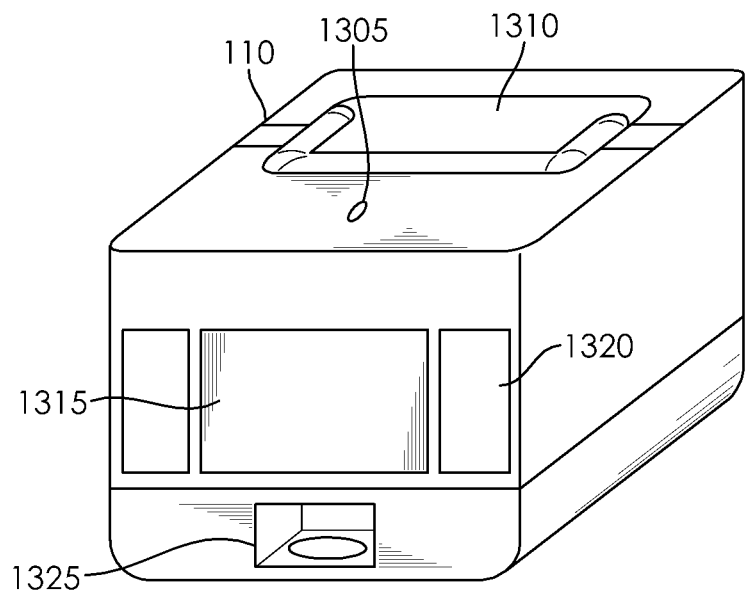
FIGS. 13A-13B depict perspective views of an exemplary connected pill dispenser.
Figure 13B:
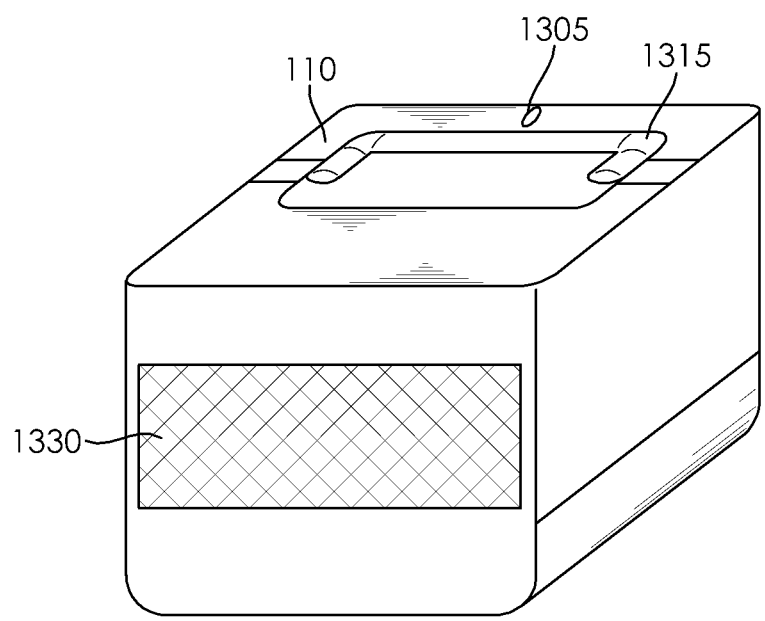

FIG. 12 depicts an exemplary conceptual diagram illustrating NucleusRx components and interactions to enhance a patient's medication adherence. In FIG. 12, the NucleusRx connected pill dispenser 110 collaborates with the pharmacy server 150 and the NucleusRx Patient/Caregiver mobile app on the mobile device 130. In the depicted example, the NucleusRx connected pill dispenser 110 alerts the pharmacy server 150 of pill quantity and notifies of compliance for payers and doctors. In the illustrated example, the NucleusRx connected pill dispenser 110 provides dose reminders to patients and compliance alerts to patients and caregivers. In the depicted example, the NucleusRx Patient/Caregiver mobile app enables remote adjustment of doses per script in the NucleusRx connected pill dispenser 110 and communication between a pharmacist and patients/caregivers. In some exemplary scenarios, if a patient/caregiver does not respond to a timed dispense of medication after a time window set by the pharmacist, a missed dose may not be dispensed until time for next dosing to avoid multiple doses within a short interval contrary to the prescribed dosing interval. Some embodiments may include a pre-set time window to authenticate and dispense meds. In an illustrative example, if the patient/caregiver does not respond within the given time window, the meds may not be dispensed and the event may be noted as "missed dose." For example, if the patient/caregiver successfully authenticates him/herself to dispense doses, but the machine falters, the event may be recorded as an unsuccessful/erroneous dispense. In various implementations, the services provided by an embodiment NucleusRx system may include, for example:

a) An auto alert from response data if any collected data is out of range set by the MD for specific patient condition b) An emergency alert by patient/caregiver if any emergency arises on patients immediate health c) Summary of compliance with 'out of expected range data' (for example, <90% compliance on intake of medicine, out of range home measured response data, any unexpected emergency health data) sent to Physician (primary) or pharmacist (secondary) for any immediate need of response by MD d) If any dose adjustment is needed or change of medication needed, MD will send new Rx to pharmacist attention who will home deliver such changed medication on dispensing tray e) Pharmacist Notifies MD and patient/caregiver of such changes FIGS. 13A-13B depict perspective views of an exemplary connected pill dispenser. In FIG. 13A, the exemplary connected pill dispenser 110 front perspective view includes the finger print scanner 1305. In the depicted embodiment, the carry handle 1310 is illustrated in an exemplary closed storage configuration. In the illustrated embodiment, the connected pill dispenser front panel includes the touchscreen display 1315 and the speaker grill 1320. In the depicted embodiment, the connected pill dispenser front panel includes the dispenser chute 1325. In the illustrated example, the dispenser chute 1325 retains the depicted pill. In FIG. 13B, the exemplary connected pill dispenser 110 rear perspective view includes the object tray door 1330.

Figure 14A:
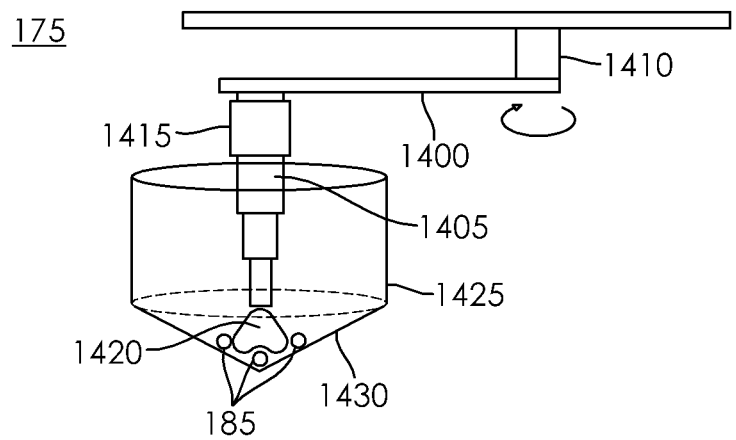
FIGS. 14A-14B depict perspective views of an exemplary connected pill dispenser robotic arm.
Figure 14B:
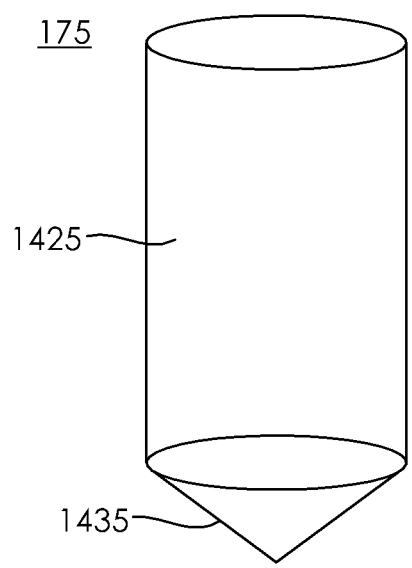

In various embodiment designs, advantageous functions of the exemplary connected pill dispenser 110 depicted by FIGS. 13A-13B may include storing a number of different types of pills, and automatically dispensing the pills to patients, in process steps such as described in the following non-limiting illustrative examples:

i) Generate visual and sound reminders when the medications are due based on pre-programmed schedules, and medication reminders can be given via the mobile app installed on patient/caregiver's mobile or wearable devices ii) Allow patients to trigger release of the pills by identifying themselves. The identification methods could be any of the following techniques:
 (1) finger print scanner (biometric)
 (2) retina scanner (biometric)
 (3) voice identification (artificial intelligence)
 (4) image identification (computer vision)

iii) The device also allows authorized caregivers to ID themselves and trigger release of the patients' meds when the patients are incapable of using the device.

iv) Within the time threshold for dispense (for example, within an hour of the first reminder) and a positive patient identification, the device dispenses the pills as per programs (for example, 1 of pill A, 2 of pill B, 1 of pill C).

v) When the pills are dispensed within the pre-defined time threshold, an event is generated indicating positive adherence for the particular dose vi) The patients are further directed by the device to take the pills such that it can capture the image. A real-time video and image analysis shall be performed utilizing computer vision and machine learning techniques to identify whether or not the patients actually took the medication. This event shall provide a high degree of positive adherence for the particular dose.

vii) If a dose is missed (that is, the patients or the caregivers do not trigger releases within the time threshold), an event is generated indicating negative adherence for that particular dose viii) Further, the device will also act as a hub for reading vital signs through wearable gadgets worn by the patients, and communicating them to central server for storing and forwarding to interested parties, such as, doctor's office or the caregiver.

ix) In some embodiments, the change in patient parameters and vital signs read from the wearable devices would determine even higher degree of compliance in addition to a positive dispensing event and/or the image/video/voice analysis Connected Pill Dispenser Construction The embodiment connected pill dispenser 110 depicted by FIGS. 13A-13B may include one or more of the following functions:

a. An electro-mechanical robotic arm for picking and placing pills b. A specially designed removable pill tray that holds multiple pill containers (referred to as bins) to facilitate various pills of variable sizes and shapes.

c. The removable pill tray may be equipped with an electro-mechanical locking mechanism for opening, closing and replacing of the pill tray, and may be controlled by the pharmacists or the caregivers via local or remote interface.

d. A tamper-resistant sensor may monitor against events where the device or the lock to the pill tray is tampered (for example, to facilitate prevention against opioid abuse or overdosing)

e. A pill dispense chute where the pills may be dispensed for retrieval and consumption by the patients f. A digital touchscreen interface to control the device, which may have configurable dashboard to allow interfaces for the patient, caregiver and the pharmacist.
 The screen may be capable of turning into a video screen for video communication between the patient, caregiver, pharmacist and the doctor g. A microphone to enable voice communication h. A speaker system for the device to play sound (for example, voice communication, Alexa/Siri/Google voice, instructions, music and anything else that shall be programmed)

i. A cellular modem interface may be configured as the primary connectivity option to connect with the internet in a secured fashion j. A WiFi module may be configured as a backup connectivity option to connect to the internet k. Bluetooth or other form of NFC type of communication modules may be configured to communicate with wearable sensors to measure patients' vital statistics, as well as to another mobile device in order to configure the connected pill dispenser l. An interface to tether with the popular voice activated systems, such as, Amazon Alexa, Apple Siri, Google Home etc.

m. A micro-controller unit (MCU) or a micro-processor unit (MPU) that will facilitate the following functions
 Central computing functions to function the device
 Controller for the robotics arm
 Controller for the peripherals (such as, OLED/LCD touchscreen display, microphone, speaker, biometric sensors-e.g. touch sensor)
 Communication modules-cellular module, WiFi module, blue-tooth or other near-field communication modules Robotic Arm Various embodiment connected pill dispenser 110 designs may include a programmable robotics arm that is particularly designed to pick pills of varied size and shape. The arm is small enough to fit in a container that can be easily portable by the users. In illustrative non-limiting examples, various robotic arm implementations may include features such as the following:

A special robotic suction gripper to be able to pick pills of varied size, shape and weight (FIGS. 14A-14B)

In various embodiments, the connected pill dispenser 110 may include a center core design (FIG. 20), where the stem or the core can move by substantially 360 degrees on the horizontal plane in order to position the robotic arm on the desired pill bin. In some embodiment implementations, the robotic arm with the gripper may be configured to move up and down on the vertical plane such that the robotic arm can be positioned to grip pills at the upper level of a full bin, as well as, to go down the pill bin when the pills are at the bottom of the bin. Such a design works for both replaceable pill tray (FIG. 16) and fixed pill tray (FIG. 17) designs.

Pill Container Tray

Pill containers and bins are designed to facilitate simple movements of the robotic arm to be able to pick pills 1. The bins are shaped conically at the bottom such that the arm can always pick from the center of the bins. Due to the conical shape, the pills naturally gravitate towards the center of the bins and facilitate easy picking till the last pill remaining in the bins (FIGS. 14A-14B).
2. Introduce tapered-bottom pill bottles (FIGS. 14A-14B) so individual pill bins can be replaced, instead of porting and replacing the entire pill tray.
3. A special shape of bin designed for larger pills such that the pill comes out one at a time from the bottom of the bins. In this case, the robotic arm picks the pills from the floor right adjacent to the special bin where the pills are individually dispensed.
4. Replaceable pill container tray (FIG. 16): the pill container tray is designed such a way that it can be easily ejected and replaced from the connected pill dispenser without compromising the pill bin positions for the robotic arm to operate. In the depicted example, the replaceable pill container tray wraps around the center core of the device that constitutes the stem of the robotic arm. To maximize space, the exemplary tray includes a mix of both narrow cylindrical containers for small pills, and large cylindrical containers for large pills.
5. Fixed pill container tray (FIG. 17): the fixed pill container tray is designed to wrap around the stem of the robotic arm. The fixed pill container tray may be configured to have the capacity to hold a higher number of individual pills than its replaceable counterpart described with reference to FIG. 16. In an illustrative example, the cylindrical pill containers are of the same shape and size to facilitate no restrictions on the pill size and shape the patients can choose to take.

Software Systems

Software to Manage Personalized Medicine

Utilizing the web portal or the mobile application, NucleusRX may be configured for the doctor's office to monitor the individual patients directly and regulate dosage as needed. This may be achieved with steps such as described in the following illustrative non-limiting examples:

1. The device software may push the following events as frequently as necessary to the central cloud server
   a. Patient's vitals collected from wearable devices worn by the patients as follows, but not limited to
      i. Body temperature
      ii. Blood pressure
      iii. Heart rate
      iv. EKG
      v. Blood oxygen level (SPO2)
      vi. Blood sugar level
      vii. Sleep pattern
      viii. Exercise information
   b. Information of the programmed medicine
   c. Records of medicine compliance
2. The web portal may allow doctor's office to set patient-specific rules based on patient's conditions and vitals. The software may alert the doctor's office by any of the below methods per the preset patient-specific rules:
   a. Visual and sound alerts on the mobile app and desktop portal based on the level of urgencies preset by the doctor's office for individual patient
   b. Text message to designated phone numbers
   c. Email messages
3. Based on the alert the doctor's office could take actions as below—
   a. Adjust dosage of medicine remotely. The device may automatically dispense pills according to the adjusted dosage. Pharmacist may be notified of the change. In some scenarios, a change of dose may require change of pills in the dispensing tray. Hence any changes in medication or even dose have to be performed by the pharmacist to patient at the direction of physician. For existing pills, the pharmacist does not need to perform the change, therefore notification only will suffice. For new pills, a pharmacist may have to intervene. In response to intervention by the pharmacist, the software may identify such actions based on the change of script.
   b. Establish communication with the patient or the caregiver to discuss conditions and decide on the next course of action:
      i. Video communication with the patient
      ii. Messaging with the patients or the caregiver using the mobile app
      iii. Phone call to the patient or the caregiver using web portal's inbuilt Web-RTC feature or mobile apps calling feature Based on patients observed vitals over a pre-determined period of time, the software can make determination of the patient's health and will generate reports on a periodic basis. Doctors may have the ability to approve such reports before they get released to any other interested parties. For example, reports can be made available to the patients as well as the insurance companies to evaluate improvement or degradation of the patients' conditions. NucleusRX may maintain, within regulatory guideline where appropriate, such reports in a database for the purpose of 3rd party utilization and monetization.

Secured Communication Channel

The NucleusRX device may be capable of messaging, voice and video communications. However, per the patient, or the caregiver's preference, s/he can choose to use her/his smart phone to communicate with the eco-system of providers. For example, the voice or the video communication from the doctor's office may follow patient's choice of device-smart phone or wearable device or the connected pill dispenser. In illustrative, non-limiting examples, the software may be capable of
a. configuring patients choice of devices and order for the choice of communication
b. creating secured channel for communication between the providers (doctors, pharmacists) and the patients or caregiver
c. directing the established communication from the provider to the choice of patient's device in a prioritized fashion. For example, doctor's office may be able to make a WebRTC based call to the patient's smart phone or the wearable device without having to choose one or the other, or without having to know where the call will be directed to. Such a WebRTC based call may occur based on pre-configuration and the choice made by the patient.

Pill Database and Scanning

In an illustrative, non-limiting example, the software system may be capable of maintaining a dynamic database of available pills in the market and their meta information, such as-color, weight, shape, and other producer and production related information, such as batch information.

The pharmacists may be able to scan medicines that may be filled in a patient's dispenser and based on the meta information, the software may direct the pharmacist to fill the pill bins and automatically update the pill information for the particular bin. Once the meds are all scanned and filled in their respective pill bins, the software may guide the pharmacists to schedule them per the doctor's prescription.

The system may allow doctor's office to identify individual patient and write script for that patient utilizing NucleusRX's web portal or the mobile app. In some examples, when the pharmacists pull the script and scan medication to fill in the pill bin, all he or she will have to do is to make sure the right pill bins are associated with doctor's script and schedule. This process will make the pharmacist's job efficient and less error-prone.

With a search on the web portal or the mobile device, the doctors or the pharmacists can track any patients within the NucleusRX system that may be taking any pills. In such an illustrative example, any pills with safety issues or problems (for example, pills made in a particular batch of production that may be defective) can be localized to patients utilizing the NucleusRX system. This feature may address an overall safety risk from such production issues or prevention of usage of a drug distributed in a malicious fashion, such as, for example, counterfeit drugs.

Patient Behavior Management

Managing patients' behavior towards medication adherence is an integral part of the design since reminders and automatic management of the medication are not enough to help with non-compliance of the patients. The following techniques shall be constituted in order to gamify the system such that patients are nudged towards medicine compliance:

Personalized Medication Reminder

Medication reminder by the device shall constitute of techniques such as, playing favorite music when a dose is due, or having the voice of a favorite person (for example, spouse, kids, grandchildren, or a friend) announce when it is time for the meds. Patients choosing to get reminded by the mobile application can have a favorite voice reminder or a combination of a preferred sound and a visual reminder utilizing a favorite image.

Social Gamification Via Mobile App

Using various NucleusRX mobile app designs, the patients may be able to find and follow friends and relatives to keep track of each other's health progress and medication adherence. For example, in some implementations, upon patient's choosing, the software may notify the follower via mobile app that the patient has taken his/her doses, which can turn into an emoji/sign indicating a "kudo" or "like" by the patient's followers. Similarly, a missed dose may result into an emoji/sign indicating an encouragement for compliance.

Reward System

In some implementations, every time a patient dispenses the meds, the software may record the event and assign the patient a point. A missed dose may result in a negative point. This may tally up to a weekly/monthly total target point. In an illustrative example, when an exemplary target point is met, the caregiver, the pharmacist or the doctor's office can send encouraging "canned" messages or custom messages via the display of the device, by messaging through the mobile app, or by making a phone call or text. Similarly, a missed goal may be greeted by further encouragement such that the patient would try his/her best to adhere to the medication regime.

The Data

The data from the device, such as types of medications, refill frequencies, adherence information, patients' vital statistics, patients' medical information, and the like, may be stored on the cloud based on patients' consent, as well as, when applicable, regulatory guidelines. In some scenarios illustrative of various embodiment implementations' design or usage, the stored information may benefit the healthcare industry in many different ways, for example and not limited to, as follows:

Assist with clinical studies

Insights on how to improve the personalized medicine for a greater patient outcome Study patient behavior and how to increase medical adherence Information for the insurance providers to learn about various aspects of the overall patient management such that they can work towards newer reimbursement models with a focus on keeping the healthcare cost low Insights on patients recovery and outcome based on many factors such as, medical adherence, combinations of pills taken, demographics, etc.

Business Models

In illustrative, non-limiting examples, various business models are disclosed, including a B2B INDIRECT, B2B DIRECT, and B2C DIRECT/INDIRECT business model. An embodiment connected pill dispenser may implement various business model features. Some embodiment business model designs may include features implemented via a connected pill dispenser design.

B2B Indirect a. Via the Pharmacies (Medicare/Medicaid/Insurance pays):
   In an illustrative example, it is an object of such a model to incentivize pharmacies to contribute towards the medicine adherence of the patients. For example, a pharmacy specializing in serving drugs for medical conditions and having an established (or willing to establish) home delivery model can take advantage of this business model.
   In an illustrative example, a new Medicare/Medicaid/Insurance (for example, the payer community) code for the eco-system of providers may be created for such a service model, for personalized and preventive care, such that the payer community reimburses the cost of the devices, device support and pharmacists' services.
   Based on patients' condition and adherence requirements, doctors may prescribe the connected pill dispenser (that is, the device) to the patients. Pharmacies may fulfill the prescription by filling in the pills and programming the prescription in a new device for the patients. The patients or the caregiver may carry the device home and stay connected by plugging into an electrical outlet. The device may remind patients of the doses, collect adherence events per dispensing of the pills, and inform the pharmacists when the supply runs low.
   In some designs, the pharmacists may replenish the medicine supply when electronically notified by the device and charge the payer for the meds. Various device implementations may collect the compliance and adherence report, and send the compliance and adherence report to the doctors' offices or to the payers, as necessary. The payers may reimburse the pharmacists for their services. In some scenarios, this facilitation may help the pharmacists earn a service fee on top of the slim margin they may earn by dispensing medicine for the patients.
b. New monetization model for the physicians (Medicare/Medicaid/Insurance pays): Doctors may monitor patients with illnesses on a 24×7 basis utilizing technology. In various embodiments, the patients' vital information and medicine adherence report may be sent to doctors on a dynamic basis, for example, triggered on-demand in response to alerts. Various examples may generate alerts and trigger sending vital information and medicine adherence reports to doctors, according to patients' preset thresholds of vital signs and adherence factors. In an illustrative example, reports may be generated utilizing communication of choice (mobile application, email, phone call, text, and visual notification via desktop application). The doctor may intervene as necessary to manage the patient condition. For example—
  i) The doctor may simply adjust the medicine doses according to patient's condition remotely via mobile application or the desktop application, which may include securely accessing the patient's medicine profile.
  ii) The doctor may request via the NucleusRX mobile or desktop application, or via a traditional method of calling into the designated pharmacy for a change of medicine-for example, replace a certain medicine, or add a new drug in the patient's prescription. Accordingly, the pharmacy physically delivers the medicine to the patient and fills the NucleusRX connected pill dispenser. The patient or caregiver may choose to bring the connected pill dispenser or the pill tray to the pharmacy, if allowed to manage the connected pill dispenser, for adjustment of medicines. The pharmacy may reprogram the change of prescription.
  iii) A doctor or nurse may choose to have a telephone call or a video call with the patient by directly reaching to the NucleusRX medical hub. The patient may utilize the NucleusRX's inbuilt calling/video-calling features to have such communications.
  iv) A doctor or nurse may choose to have a communication with the caregiver to discuss patient's condition and prescribe the next course of action for the patient to take. Such communication can happen via a telephone call, text, or alerts/messaging features of the caregiver mobile application.

In some examples, a new Medicare/Medicaid/Insurance code for the doctors may be created for such a service model for personalized and preventive care. Such business model will be a departure from the traditional model, where the doctor-patient relationship is transaction based, versus a continuous service-based model. While this new continuous service-based model will allow doctors to have a new form of revenue stream, the overall idea is to enable personalized medicine by better monitoring, medicine adherence, and dynamic adjustments of medicine, such that patients' overall health improves, while the overall long-term health-care cost goes down.

B2B Direct
  a. Patient monitoring by the hospitals (hospitals pays)-in order to reduce readmission rate, the hospitals may require remote patient monitoring and monitoring of medicine adherence by the patient. In such a model, the hospitals may procure the NucleusRX device and send the device with discharged patients having had an illness where the chance of readmission is high. NucleusRX may provide mobile application and web interface access for the hospitals to manage the devices remotely, and get patients' reports for a period of time deemed necessary for the hospitals to keep a patient on this program. In an illustrative example, a hospital may purchase the devices and associated support services one time, and rotate the device until the end of the device service life. Alternatively, a hospital may rent the device for a distributor or directly from NucleusRX. The rental fee may cover the cost of the device, cost of software seats, and associated services.
  b. Patient monitoring by rehabilitation centers (rehab facilities pays, or Medicare/Medicaid/Insurance pays): Certain rehab centers are compelled to monitor patients' drug intake regimen closely (for example, to facilitate prevention of opioid overdose). In such cases, rehab centers may provide devices on a temporary basis to the patients and regulate as well as monitor their drug usage. A similar business model as in the case of hospitals (2.a) may exist to fulfill the business relationship in this model.
  c. Home healthcare facilities (service provider pays)—In order to provide differentiated services, home healthcare services companies have the opportunity to use NucleusRX devices and services. Again, a similar business model may be made available to such home healthcare providers.
  d. Clinical studies (pharmaceutical companies pay)—For a higher degree of accuracy in clinical studies, understanding the subject patients' adherence as well as nudging them to taking the required medicine is critical. NucleusRX can assist in such cases. The same device can be used for such studies, along with target software specifications to remotely manage patients and doses required for clinical studies use cases.

B2C Direct/Indirect
  a. Direct sell to patients or caregivers (patient or caregiver pays): This is an existing model where the patients and/or caregiver purchases the device, software seats and support service directly. In order to compete in the marketplace, the device features and services may be customized and differentiated to create compelling value-add for the consumers.
  b. Indirect sell to patients or caregivers via pharmacies, doctor's offices etc. (patient or caregiver pays): In this model, the patients or the caregivers can purchase the device, software seats and associated support services indirectly from their pharmacies or doctors.

FIGS. 14A-14B depict perspective views of an exemplary connected pill dispenser robotic arm. In FIG. 14A, the exemplary connected pill dispenser robotic arm 175 includes the telescopic arms 1400 and 1405 configured to retract and expand. In the depicted embodiment, the exemplary connected pill dispenser robotic arm 175 is pivotally secured at the first swivel 1410 to rotate 360 degrees in thirteen positions about the depicted first axis. In the illustrated embodiment, the telescopic arm 1405 is pivotally secured at the second swivel 1415 to rotate about a second axis distal from the first axis. In the illustrated embodiment, the telescopic arm 1405 includes the suction grip 1420 configured to extend into the object bin 1425 to grab one or more payload 1430 item. In the depicted example, each payload 1430 item is a medication dose 185. In the illustrated example, each medication dose 185 is a pill. In FIG. 14B, the depicted object bin 1425 includes the tapered bottom 1435.

FIGS. 15A-15H depict side views of an exemplary connected pill dispenser robotic arm suction grip in various illustrative operational configurations. In FIG. 15A, the exemplary telescopic arm 1405 directly grabs the medication dose 185 with a suction nozzle configured in the telescopic arm 1405. In the illustrative operational configurations depicted by FIGS. 15B-15H, the exemplary telescopic arm 1405 includes the suction grip 1420 configured to aid grabbing by the suction nozzle configured in the telescopic arm 1405 an individual medication dose 185 having varied size or shape, presented in varied orientations.

Figure 16:
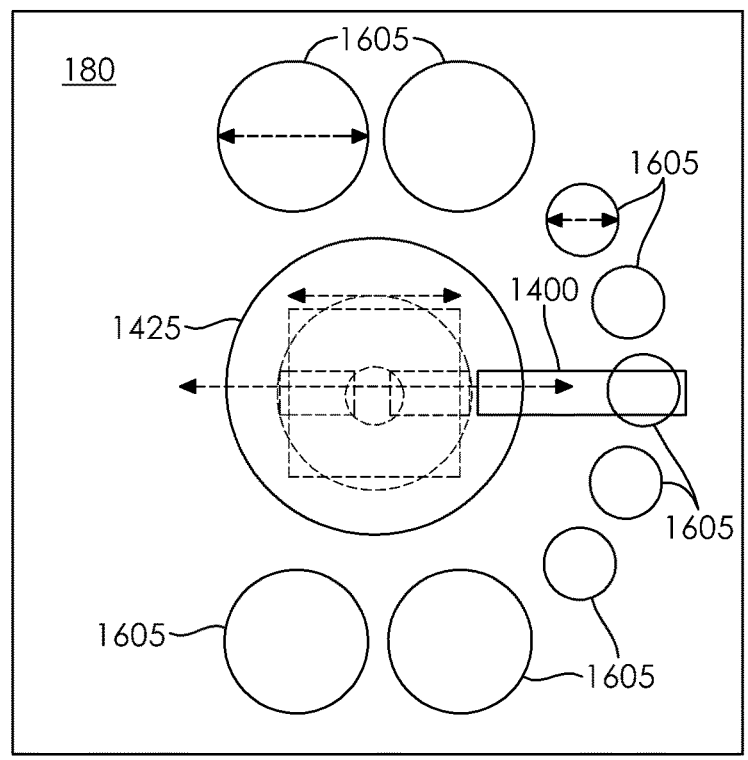
FIG. 16 depicts an exemplary replaceable pill container design.

FIG. 16 depicts an exemplary replaceable pill container design. In FIG. 16, the exemplary replaceable pill container 180 includes the pill bins 1605 having a variety of sizes in an illustrative replaceable configuration. In the depicted embodiment, the pill container 180 is configured with the connected pill dispenser telescopic arm 1400 pivotally secured to access the object bin 1425 and the pill bins 1605.

Figure 17:
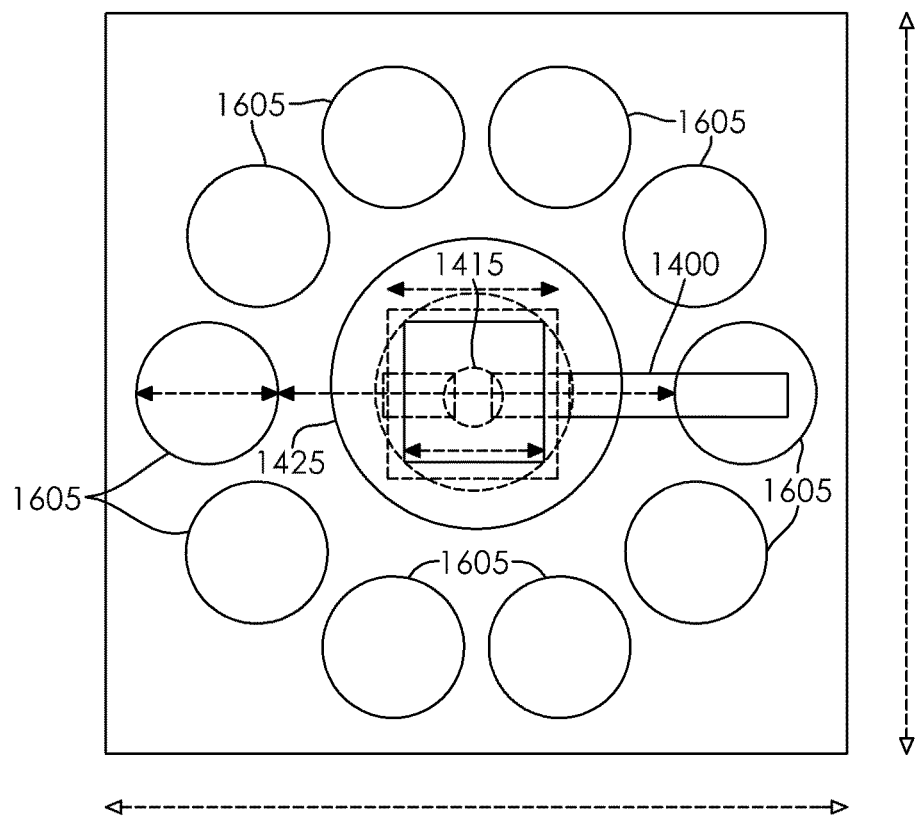
FIG. 17 depicts an exemplary fixed pill container design.

FIG. 17 depicts an exemplary fixed pill container design. In FIG. 17, the exemplary fixed pill container includes the pill bins 1605 in an illustrative fixed configuration. In the depicted embodiment, the pill container is configured with the connected pill dispenser telescopic arm 1400 pivotally secured at the second swivel 1415 to access the object bin 1425 and the pill bins 1605.

Figure 18A:
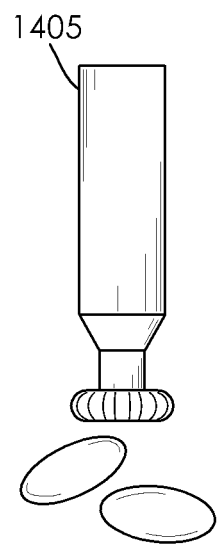
FIGS. 18A-18C together depict operational views of an exemplary vacuum suction gripper including a tube-shaped rubber skirt configured around the suction nozzle.
Figure 18B:
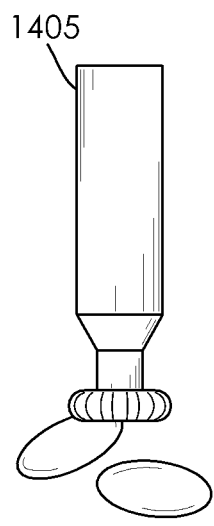
Figure 18C:
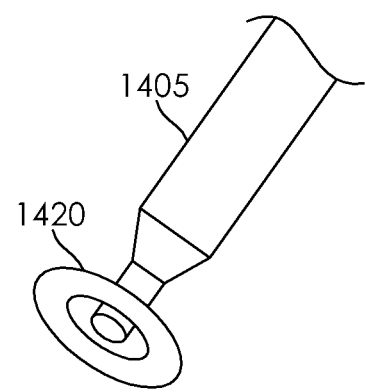

FIGS. 18A-18C together depict operational views of an exemplary vacuum suction gripper including a tube-shaped rubber skirt configured around the suction nozzle. In the embodiment depicted by FIGS. 18A-18C, the tube-shaped rubber skirt configured around the suction nozzle is adapted to create a suction vacuum around the edges of the elongated pills. In an illustrative example, the inner surface curvature of the tube-shaped skirt urges the elongated pills toward the gripper based on rotationally aligning the pills with the gripper suction nozzle force, thereby enhancing the ability of the gripper to grip pills of diverse sizes and shapes. In FIG. 18A, the exemplary gripper configured in the telescopic arm 1405 is depicted approaching the pill. In FIG. 18B, the gripper slightly pushes against the pill with the tube and creates a vacuum suction to grip the pill. In FIG. 18C, the bottom of the tube skirt 1420 is depicted after release of the pill into a dispensing chute.

Figure 19A:
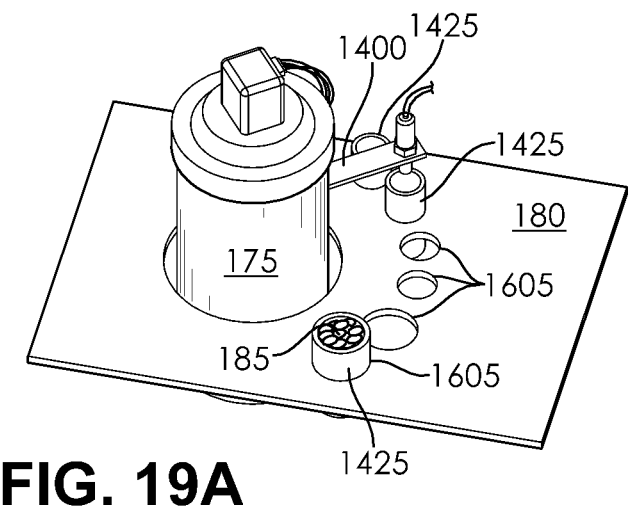
FIGS. 19A-19K together depict operational top perspective views of an exemplary connected pill dispenser robotic arm dispensing a medication dose, based on gripping the medication retained by an embodiment pill container and releasing the dose into an exemplary dispensing chute.
Figure 19B:
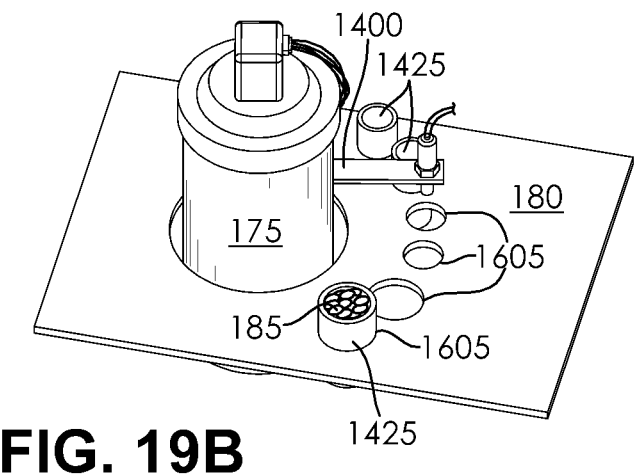
Figure 19C:
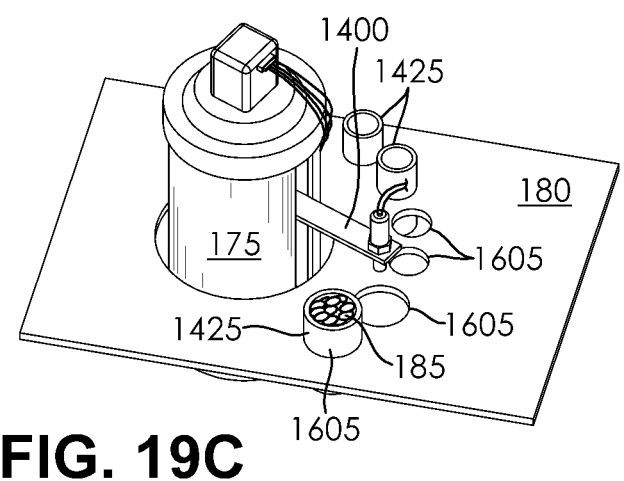
Figure 19D:
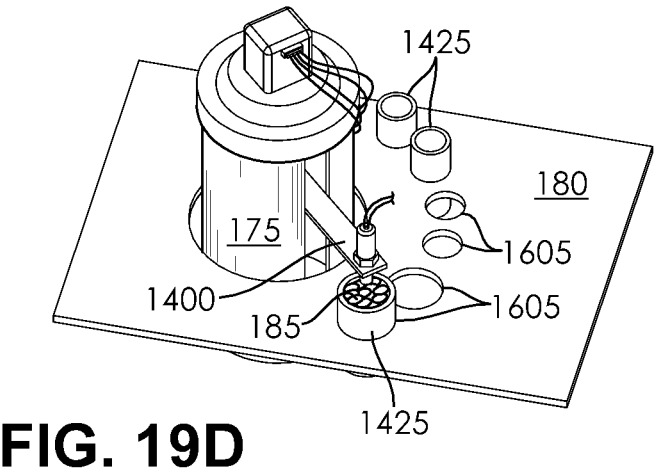
Figure 19E:
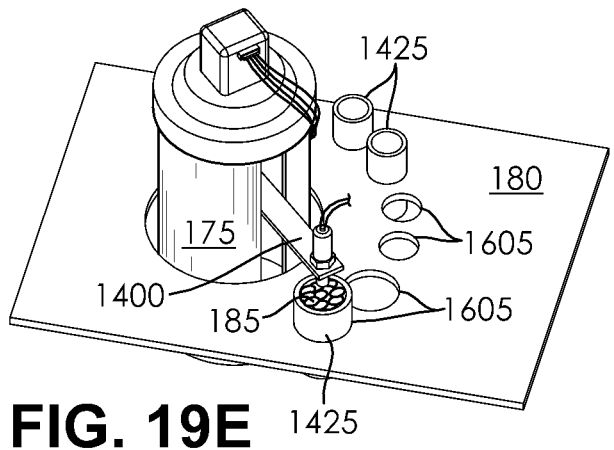
Figure 19F:
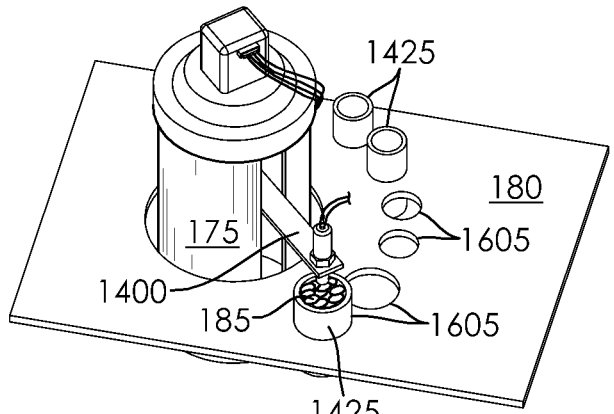
Figure 19G:
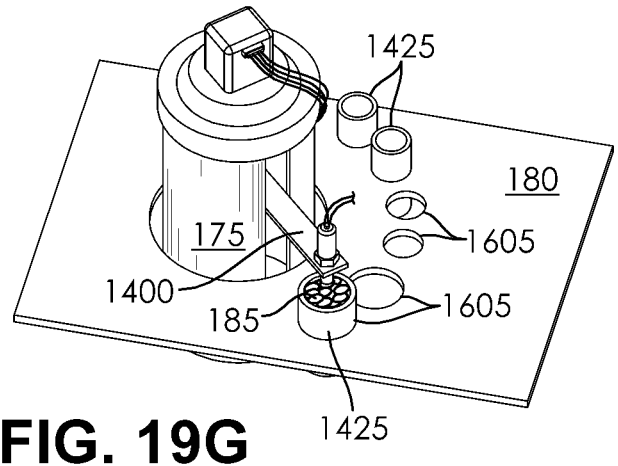
Figure 19H:
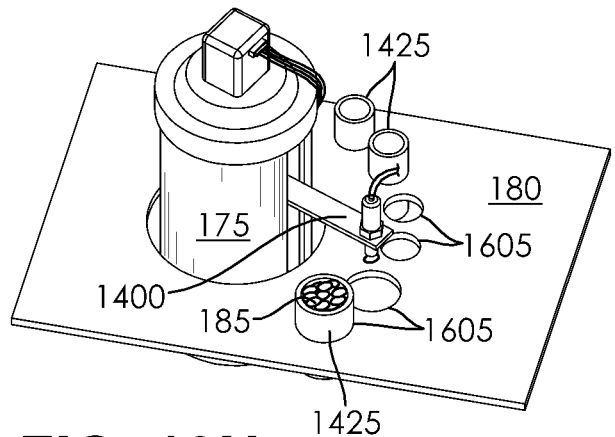
Figure 19I:
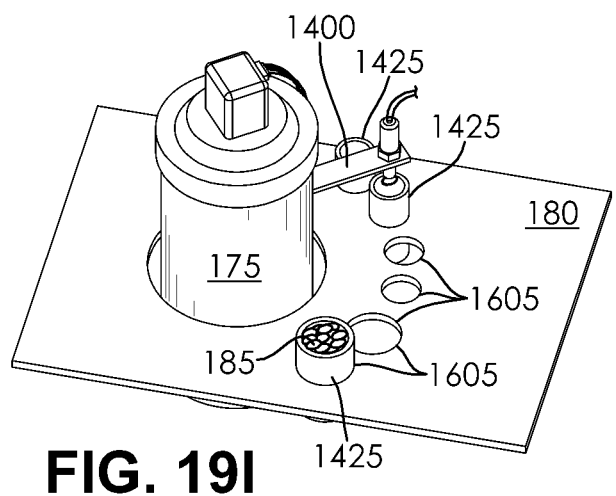
Figure 19J:
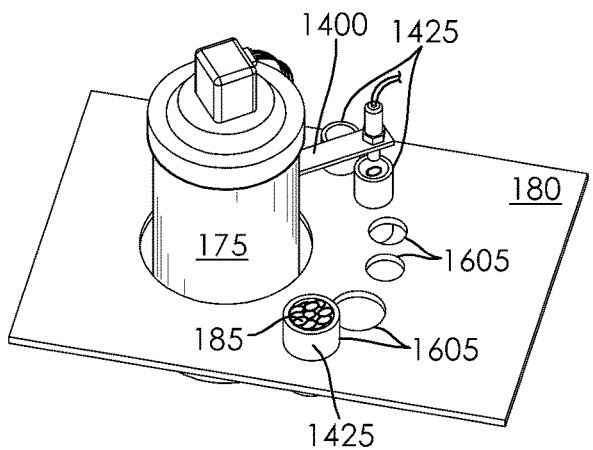
Figure 19K:
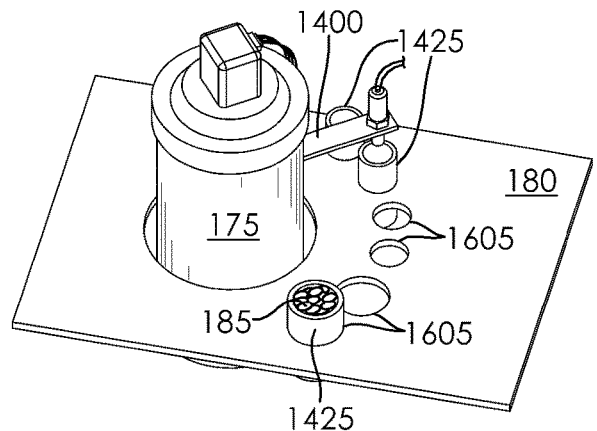

FIGS. 19A-19K together depict operational top perspective views of an exemplary connected pill dispenser robotic arm dispensing a medication dose, based on gripping the medication retained by an embodiment pill container and releasing the dose into an exemplary dispensing chute. In FIG. 19A, the exemplary connected pill dispenser is depicted in an illustrative medication dose dispensing starting mode with the robotic arm 175 including the telescopic arm 1400 disposed in a first position distal from the medication dose 185 retained in the exemplary object bin 1425 by the pill bin 1605. In FIG. 19B, the exemplary connected pill dispenser robotic arm 175 has begun to move toward the medication dose 185. In FIG. 19C, the exemplary connected pill dispenser robotic arm 175 continues in motion to the medication dose 185. In FIG. 19D, the exemplary connected pill dispenser robotic arm 175 motion stops when the telescopic arm 1400 reaches the medication dose 185. In FIG. 19E, the connected pill dispenser robotic arm 175 descends to position the gripper and suction nozzle for access to the medication dose 185. In FIG. 19F, the connected pill dispenser robotic arm 175 gripper securely grabs the medication dose 185 based on vacuum suction from the nozzle. In FIG. 19G, the connected pill dispenser robotic arm 175 ascends to position the gripper to transport the medication dose 185 to a dispensing chute. In FIG. 19H, the exemplary connected pill dispenser robotic arm 175 gripping the medication dose 185 has begun to move toward the dispensing chute. In FIG. 19I, the exemplary connected pill dispenser robotic arm 175 gripping the medication dose 185 continues in motion toward the dispensing chute. In FIG. 19J, the exemplary connected pill dispenser robotic arm 175 gripping the medication dose 185 has reached the dispensing chute in a second illustrative dispensing position distal from the medication dose 185 retained by the exemplary pill container 180. In FIG. 19K, the exemplary connected pill dispenser robotic arm 175 releases the medication dose 185 into the dispensing chute.

Figure 20:
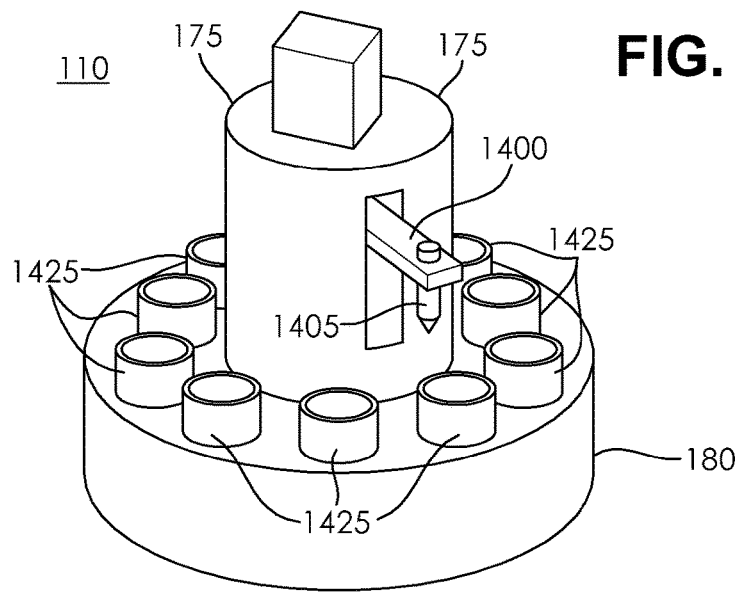
FIG. 20 depicts a top perspective view of an exemplary center core robotic arm design.

FIG. 20 depicts a top perspective view of an exemplary center core robotic arm design. In the embodiment depicted by FIG. 20, the connected pill dispenser 110 includes a center core robotic arm 175 design, wherein the stem or the core can move by substantially 360 degrees on the horizontal plane in order to position the robotic arm 175 for access to the desired object bin 1425. Each object bin may be retained by a pill bin 1605, depicted at least by FIGS. 16 and 19A-19K. In the illustrated embodiment, the robotic arm 175 including the telescopic arm 1400 and the telescopic arm 1405 configured with the gripper is configured to move up and down on the vertical plane such that the robotic arm 175 can be positioned to grip pills at the upper level of a full object bin 1425, as well as, to go down into the object bin 1425 when any pill may be at the bottom of the bin. The depicted design is applicable with replaceable pill tray (FIG. 16) and fixed pill tray (FIG. 17) designs, and other pill tray designs. In the center-core robotic arm design example depicted by FIG. 20, the vertical movement of the arm is controlled by a screw mechanism at the center core, instead of the telescopic concept depicted by FIG. 14A. In the depicted center-core design illustrated by FIG. 20, the telescopic arm 1400 may move vertically as well as in a circular fashion on the horizontal plane for positioning on the desired pill vial/bin. Further, the picking arm will have flexibility to position the picking grip in order to pick pills situated in various angles within the vials. In various implementations, a suction gripper as depicted, for example, by FIG. 15A may be used to grip and pick pills from the vials.

Although various embodiments have been described with reference to the Figures, other embodiments are possible. For example, various embodiments may be referred to as NucleusRx: The Connected Pill Dispenser. In some embodiments, an exemplary NucleusRx Connected Pill Dispenser may be a connected pill dispenser designed for use by a patient with an illness. Various embodiments include an internet-connected electro-mechanical connected pill dispenser that stores patients' prescription and non-prescription pills; alerts patients and/or caregivers when doses are due; and dispenses prescribed doses with minimal intervention from the patients. Some exemplary devices may be designed to create value by improving patients' adherence and compliance to medication regime by use of technology as well as behavior management techniques. In an illustrative example, some embodiments can be remotely and dynamically programmed by the pharmacists or the caregivers based on prescriptions from patients' physicians.

An exemplary connected pill dispenser 110 (depicted at least by FIGS. 1, 2, 3, 11, 12, and 13A-13B) implementation may be designed to perform various operations based on sensor data. The sensor data may be acquired by one or more sensor operably coupled with a processor configured to operate with the connected pill dispenser 110. The one or more sensor operably coupled with a processor configured in the connected pill dispenser 110 may include a sensor of various types. The operations performed by an exemplary connected pill dispenser 110 based on sensor data may include, for example, capturing baseline or reference data for comparison with live sensor data, capturing reference data for configuring or training a machine learning or artificial intelligence model or structure to create predictive analytic output representative of a patient outcome based on sensor data, measuring patient physiological parameters, adjusting a dose, determining patient condition, determining medication adherence, or adapting the operation of the connected pill dispenser 110, in response to the sensor data processed by the connected pill dispenser 110.

For example, a sensor configured to operate with an exemplary connected pill dispenser 110 may be a device-centric sensor, or a patient-centric sensor. A device-centric sensor may be, for example, a sensor configured in the connected pill dispenser 110 to acquire data associated with the device or the patient. A device-centric sensor may be a sensor configured in the device to detect tampering, to determine when a patient has opened or closed a dispensing chute access door, or a camera configured in the device to capture images of patient medication consumption activity. A patient-centric sensor may be, for example, a sensor configured in the connected pill dispenser 110 or worn by a patient, to acquire data associated with a patient. A patient-centric sensor may be a physiological sensor designed to transduce a patient physiological response acquired by the sensor to a signal data package consumable by a processor. An exemplary signal data package may include one or more signal, noise, or other data. For example, some sensor types may include time stamps correlated with signal data, such as photographs. In any case, a sensor, or the processor, or both, nay be configured to process into useful form the signal data package emitted by the sensor, based on isolating the desired signal from the signal data package.

A device-centric sensor configured in the connected pill dispenser 110 to acquire data associated with a patient may include an image sensor, such as a still picture camera, video camera, infrared camera, time of flight camera, or other imaging device. A still picture camera may be used to capture a patient image useful for authentication, such as, for example, by facial recognition, facial biometric feature identification (for example, matching the geometry of facial features such as displacement and structure of eye sockets, nasal bridge, or mouth or lip geometries, to previously captured images of the patient). In some examples, facial identification and biometric feature identification may be augmented with distance from target data provided by a time of flight camera, permitting more accurate identification based on facial features measured with respect to facial distance from the camera.

An image sensor such as a video or still picture camera may facilitate medication adherence determination based on computer vision. For example, captured video or still images of patient activity may be analyzed by a connected pill dispenser 110 to identify images that can be correlated with or matched to image data representative of various patient activity states such as limb positions, hand positions, postures, gestures, or reflexes, associated with medication adherence. For example, a sequence of images of a patient could be captured while the patient consumes a medication dose. The captured images could be time stamped based on time of capture, to validate the timing of patient consumption activity with respect to patient-specific baseline consumption time (for example, compared with the length of time required for the patient to consume the dose in a controlled, or supervised, successful test dose). The time stamped images could be correlated to images captured of the patient consuming medication in the controlled or supervised setup operation, to validate the patient consumption of the medication dose. In some examples, an alert may be triggered, if the dose is not consumed within a threshold period of time in excess of the patient-specific baseline consumption time.

A device-centric sensor configured in the connected pill dispenser 110 to acquire data associated with a patient may include an audio sensor, such as a microphone. A microphone may be used to capture patient audio representative of patient identification or communication. For example, speaker identification techniques may be used to authenticate a patient based on audio data captured by microphone. Speaker recognition techniques may be used to transform a patient's verbally spoken words to text for processing by an exemplary connected pill dispenser 110. For example, an embodiment connected pill dispenser 110 may determine a patient condition at least in part by verbally asking a patient if they feel better or worse, if they feel warm or have chills, how many pills they swallowed, the color of the pills swallowed, or if they still have a headache. In response to such questions, a patient may verbally respond with one or more word, 'Better,' 'Warm,' 'Three,' 'Yellow,' or 'No,' and the words may be transformed to text for processing by an exemplary connected pill dispenser 110. In some examples, patient responses may be used by an embodiment connected pill dispenser 110 to interactively traverse a diagnosis or treatment determination decision tree, based on comparing patient responses with responses encoded by the tree. Various connected pill dispenser 110 designs may employ such a decision tree to prescribe medication, adjust a medication dose, recover from a missed dose, or send a notification. Such a diagnosis or treatment decision tree may be provided for use in the connected pill dispenser 110 by a healthcare or healthcare service provider, such as a doctor, payer, or pharmacy. Various connected pill dispenser 110 designs may receive diagnosis or treatment decision tree guidelines that are automatically updated when prescribing or treatment guidelines are revised by pharmaceutical companies, payers, or government regulatory agencies.

Some connected pill dispenser 110 designs may permit a patient's treating physician to customize a diagnosis or treatment decision tree to the patient. In an illustrative example, such a customized patient-specific diagnosis or treatment decision tree may include steps specific to a patient's condition, such as, for example, ensuring a patient has consumed one type of medication, before attempting to provide the patient a dose of another type of medication. Other custom steps could include, for example, determining if the patient is anxious, based on verbally asking the patient if they are anxious, and analyzing the patient verbal response; in response to determining the patient is anxious, measuring the patient's blood pressure to determine if the patient's blood pressure is within normal range; in response to determining the patient's blood pressure is above normal range, dispensing a blood pressure medication dose determined as a function of the blood pressure measurement and prescribing guidelines determined by the patient's physician; and, in response to determining the patient's blood pressure is not above normal range, dispensing an anti-anxiety medication dose prescribed by the patient's physician.

In some examples, the connected pill dispenser 110 may provide the status of traversing such a diagnosis or treatment decision tree to the patient's doctor. For example, the patient's doctor could customize a patient-specific decision tree configuring an exemplary connected pill dispenser 110 to notify the doctor immediately if the patient has a headache, the patient has consumed the prescribed blood pressure medication, and the patient has blood pressure above a predetermined minimum blood pressure level. In such an example, the doctor responding to the notification may further interact with the patient by voice or video to determine the next treatment action. In some examples, the doctor may remotely direct the exemplary connected pill dispenser 110 to dispense additional blood pressure medication, or headache medication, or both.

In various scenarios, an exemplary connected pill dispenser 110 (depicted at least by FIGS. 1, 2, 3, 11, 12, and 13A-13B) implementation may adjust a medication dose. A patient's doctor may adjust a blood pressure medication dose to be dispensed by the exemplary connected pill dispenser 110 for the next several doses, in response to the patient condition. The patient condition may be determined by the connected pill dispenser 110 based on sensor data. The doctor may change the prescription governing the dose to be dispensed by the exemplary connected pill dispenser 110 for all subsequent doses. In some examples, the exemplary connected pill dispenser 110 may be programmed and configured to autonomously adjust the dose of a particular medication specified by the doctor in a dose amount varied within limits determined by the doctor and prescribing guidelines. For example, the exemplary connected pill dispenser 110 may determine the patient condition based on sensor data, adjust a medication dose based on the patient condition, deliver the dose to the patient, and determine medication adherence based on sensor data.

Some exemplary connected pill dispenser 110 designs may adjust a medication dose in accordance with a treatment decision tree encoding dose limits depending on patient physiological parameters. For example, an exemplary connected pill dispenser 110 may measure a patient's heart rate, temperature, and blood pressure physiological parameters, determine, based on the measurements, the physiological parameters are within normal range for the patient, and the exemplary connected pill dispenser 110 may dispense a nominal amount of multiple medications, including a daily, nominal blood pressure medication dose, according to a scheduled dosing regimen. In another example, the exemplary connected pill dispenser 110 may measure a patient's heart rate, temperature, and blood pressure physiological parameters, determine, based on the measurements, the blood pressure parameter is below normal range, and dispense a reduced blood pressure medication dose, based on the low blood pressure measurement. In some examples, the exemplary connected pill dispenser 110 may substitute another medication, for example, a diuretic medication, in place of the blood pressure medication, in response to the low blood pressure measurement. Various exemplary connected pill dispenser 110 implementations may adjust the medication amount of a dose calculated as a function of a patient physiological parameter measured by a sensor, in view of dosing guidelines programmed and configured in the exemplary connected pill dispenser 110. In some examples, the patient's doctor may be notified, and manually adjust the dose. Various implementations may provide capability to perform autonomous dose adjustment by the exemplary connected pill dispenser 110, and manual dose adjustment by a healthcare professional in the treatment loop, facilitated by the exemplary connected pill dispenser 110.

In an illustrative example, an exemplary connected pill dispenser 110 may be configured as a hub for other patient-wearable sensors, data from which can be utilized to enhance determination of medication adherence. For example, an EKG monitor, blood pressure monitor, thermometer, or other patient-owned device may be wirelessly paired or connected with the connected pill dispenser 110, to provide additional and/or alternative data sources used to determine medication adherence.

In an illustrative example of automatic dose adjustment by an exemplary connected pill dispenser 110, a blood-pressure monitor could provide data to the connected pill dispenser 110 that could then automatically adjust the number or schedule of blood-pressure-controlling pills dispensed. The physician could set dose and/or schedule limits that the connected pill dispenser 110 must operate within. The connected pill dispenser 110 could report patient progress to the physician. The connected pill dispenser 110 could also report if the dispenser reaches the allowed dose and/or schedule limits to allow the physician to evaluate the patient, drug selection, and/or drug dosage.

In various scenarios, an exemplary connected pill dispenser 110 (depicted at least by FIGS. 1, 2, 3, 11, 12, and 13A-13B) implementation may determine medication adherence based on data acquired from one or more sensor. For example, an exemplary connected pill dispenser 110 design may compare captured video, audio, or image data representative of a patient's putative medication consumption activity with baseline or reference data representative of successful medication consumption, to determined medication adherence based on the comparison. Some exemplary connected pill dispenser 110 implementations may be configured with patient-specific machine learning models trained with baseline successful and unsuccessful consumption activity. In an illustrative example, such a patient-specific model may be employed to predict successful medication consumption as a function of live video, audio, or image data representative of a patient's activity attempting to consume medication. Various imaging techniques may be employed to capture the patient and dose delivery environment state before and after the putative dose event. For example, an image of a cup of water used to help swallow a pill may provide a proxy for determining if the pill was swallowed; that is, if the cup water level has declined between start of dose, and end of dose event, and the patient when asked responds they have consumed the dose, a prediction the patient consumed the dose may be made. In some examples, computer vision techniques including object tracking, motion detection, object identification, and optical flow may be employed to determine medication adherence. For example, the patient could be asked to show to the camera their hand holding the pill to be swallowed, then video could be captured of the patient moving their hand to their mouth, and showing their empty hand to the camera. In some examples, audio confirmation of the patient swallowing may be obtained by a microphone. In an illustrative example, the exemplary connected pill dispenser 110 may use object identification techniques to identify the pill in the patient's hand, to determine medication adherence based on identifying the pill and the pill location in the patient's hand. The exemplary connected pill dispenser 110 may use object tracking techniques to track and record the path of the patient's hand to the patient's mouth, the path of the patient's hand to pick up a cup of liquid from a table, move the cup to the mouth, swallow the liquid, and return the cup to the table, to determine medication adherence based on comparing the patient's hand motion to predetermined hand motion representative of a successful dose event. Various examples may validate medication adherence based on physiological sensor data; for example, if blood pressure medication is delivered to a patient, and the patient's blood pressure should be expected to decline but does not, such an event characterized in terms of an expected but not realized response in the patient's blood pressure may reduce the probability medication was consumed successfully.

Some exemplary connected pill dispenser 110 implementations may verify the patient has taken the prescribed medication dose based on a signal from a medication dose configured to wirelessly report when the dose has been ingested. The connected pill dispenser 110 may incorporate wireless connectivity directly to such a medication dose that wirelessly reports when the dose is ingested. The connected pill dispenser 110 could also incorporate wired or wireless connectivity to the monitoring devices associated with such medication doses that wirelessly signal when the doses are ingested.

In various scenarios, an exemplary connected pill dispenser 110 (depicted at least by FIGS. 1, 2, 3, 11, 12, and 13A-13B) implementation may compensate for one or more missed medication dose. As disclosed herein, an exemplary connected pill dispenser 110 may determine a patient's medication adherence to a prescribed dosing regimen using various techniques. In an illustrative example, when a patient's lack of medication adherence is determined for a specific dose by an exemplary connected pill dispenser 110, at least that dose may be considered a missed dose. In some examples, the missed dose may be skipped, and the next scheduled dose attempted by the connected pill dispenser 110 in accordance with the prescribed dosing regimen. However, an effective plan to recover from one or more missed dose may enhance patient well-being and reduce risk to patient health. In an illustrative example, different drugs may have different recommendations for how to recover after one or more missed dose, to optimize therapeutic value and reduce risk to the patient's health. In some scenarios, an exemplary connected pill dispenser 110 design may be programmed and configured with drug-specific missed dose recovery protocols based on pharmaceutical manufacturer recommendations. For example, one missed dose recovery response implemented by an exemplary connected pill dispenser 110 based on drug manufacturer recommendations may be to ignore the missed dose, and continue the normal schedule. Another response implemented by an exemplary connected pill dispenser 110 based on drug manufacturer recommendations may be to double the next dose and then return to the normal schedule. In some examples, the connected pill dispenser 110 and/or cloud may store the drug-appropriate recovery and implement the recovery automatically. Alternatively, an embodiment connected pill dispenser 110 may alert a pharmacist and/or physician to define and/or implement the appropriate recovery.

In an illustrative example, various embodiment NucleusRx implementations may facilitate better communication among the pharmacists, the doctors, the caregivers and the patients and allow for monitoring of patients' adherence and administration of the right dosage of medication, based on use of technology. For example, information gathered on patients' extended medication compliance in turn helps the payer community get visibility into the patient compliance to medication, and subsequently effectiveness of the treatment. In some examples, nudging patients adhering to the prescribed medication, and establishing strong correlation between clinical compliance and treatment effectiveness leads to a better patient outcome, and ultimately reducing the overall healthcare cost.

Various embodiment NucleusRx implementations are positioned as a solution designed with the goal of increasing patient adherence with medicine by addressing the main pain points that other competitive solutions in the market fail to capture. With the innovative use of technology and application of modern techniques of social and behavioral science, NucleusRx drastically simplifies medicine adherence for patients. In the process, it creates win-win factors for the eco-system of healthcare providers, payers and caregivers such that participation into the process rewards all eco-system players and contributes towards reduction of the overall healthcare cost.

In an illustrative example, NucleusRx's mission is to build the next generation connected healthcare technology platform that improves lives by nudging patients of various illnesses to maintain adherence to medication, leading to a better patient outcome and an overall reduction in ever-rising healthcare cost throughout the world.

According to National Council on Patient Information and Education (NCPIE)—Medication "non-adherence" (also known as "non-compliance") means not taking your medicine as prescribed according to the directions of your healthcare provider and/or the directions on the medicine label.

Lack of prescription medicine adherence and compliance can lead to unnecessary disease progression, disease complications, a lower quality of life, and even possibly premature death. Lack of prescription medicine adherence is a phenomenon that is a major contributor to ever-rising healthcare cost in the US. Approximately half of the estimated 187 million Americans who take one or more prescription medicines do not take their medications as prescribed, according to NCPIE.

The U.S. pays a high price for poor adherence: lack of medication adherence is associated with poorer health outcomes, resulting in approximately 125,000 preventable deaths a year. On a national level, avoidable medical spending (such as ER visits, hospitalizations) resulting directly from non-adherence accounts for up to $290 billion per year, or 13 percent of total healthcare expenditures. In this way, non-adherence to medicine can not only hurt individual patients, but also hurts our healthcare system as a whole.

Whether "Tips for keeping track of your medications and remembering to take them" by NCPIE (http://www.bemedwise.org/medication-safety/medication-management-adherence), or "8 Tips to Sticking to Your Medication Routine" by Food and Drugs Administration (FDA) (https://www.fda.gov/Drugs/ResourcesForYou/SpecialFeatures/ucm485545.htm)—it is increasingly challenging for patients to adhere to medicines for multiple factors as further described by NCPIE as below—"Medication "non-adherence" or "non-compliance," either intentionally or inadvertently, can include, for example: Failing to initially fill a prescription; Failing to refill a prescription; Discontinuing a medication before the course of therapy is complete; Taking more or less of a medication than prescribed; or, Taking a dose at the wrong time."

Medicine adherence is a complex issue contributed with behavioral and non-behavioral factors, costing the US healthcare system 100's of billions of dollars every year. What if there is a single solution to address majority of such issues?

Some embodiment NucleusRx implementations may include various elements, including user interface components as below:

Connected Pill Dispenser:

Various embodiment connected pill dispenser 110 designs include an electro-mechanical device, which is remotely connected to NucleusRx's central cloud server via cellular and/or WiFi connection. For example, the device may have storage capability of 10-12 different pills for 30-90 days' supply. It can be remotely programmed to schedule auto dispensing of pills. The device provides visual and sound alerts to patients or patients' caregivers when a dose is due. The device dispenses the pills in a hygienic manner (in a cup or an embedded tray) when the patient or the caregiver provides a signal (e.g. patient/caregiver enters a special code, or a biometric signal such as finger print is provided by the patient).

In some embodiments, the connected pill dispenser 110 may use a special algorithm to identify if a patient has actually taken the medication within a certain period after it is dispensed. The inputs to the algorithm are the various information it gathers, such as-time of the alert, the number of times the alerts are generated within a certain period of time, if the caregiver or the patient has dispensed medicine within a preset time after the alerts are generated etc. Other behavioral measures will be incorporated in order to get a better and accurate gauge of the adherence of medication.

Some embodiment connected pill dispenser 110 designs may be capable of managing pill counts at all times, generating alerts based on the pill counts for the pharmacy to learn about how long certain pills' supply would last for the patient. This information will be critical for the pharmacy to replenish the drug for the patient on time (that is, for example, via an auto refill reminder).

NucleusRx Web Portal:

In various embodiments, the NucleusRx web portal 165 may be designed primarily for the pharmacists to interact with the patients. Some embodiment web portal 165 implementations may enable secure access to each patient's NucleusRx dispenser and all the information related to its pill configuration, doses programming, pill counts, and patient's information.

In some web portal 165 designs, a pharmacist will be able to program the dose times as per doctor's prescription using the web portal 165 for each of the patients it serves. Based on patient's doctor's change of prescription, the pharmacist will be able to program any change of medication regime remotely and dynamically as well.

Various embodiment web portal 165 implementations provide a source for the pharmacist to get access to patient's alerts and notification, which will be individualized based on patient's needs and service plans. For example, the web portal 165 may alert the pharmacist when the pills deplete to a pre-determined level (e.g. 25% pills remaining for a refillable medication), such that pharmacist can assist the patients by pro-active scheduling for replenishment of pills and finally replenishing them on time. This also allows pharmacists to maximize their medication dispense revenue. The pharmacists can also get access to weekly/monthly/annual reporting of patient's compliance or adherence information from this portal.

In an illustrative example, a doctor's office can get access to patient's information via an embodiment NucleusRx web portal 165. This will provide the patient's medication compliance information/report, which can directly assist the doctor in assessing the efficacy or effectiveness of the prescribed medication.

Further, the payer can assume access to similar type of information for the patients they indirectly reimburse for.

NucleusRx Mobile App:

In various embodiments, the NucleusRx mobile application 135 may be designed for the patients, the caregivers, the pharmacists and the doctors. An exemplary app 135 may provide patients with information about the pills and their doses. It also synchronizes with pharmacists' portal information dynamically. In an illustrative example, an embodiment app 135 may serve as an alert center to remind patients of medication time or missed doses.

In some examples, an embodiment app 135 may allow the patients to securely communicate with the pharmacists, the caregivers and with the doctors. It further allows patients to discover friends and family utilizing the same app and create a social network in order to keep tab of each other's health progress, as well as to provide encouragement to each other via social gaming.

In an illustrative example, caregivers of the patients will have access to patient's pill adherence information. In some examples, a social aspect will be designed in the app for caregivers to encourage patients with their medication regime based on the alerts they will receive regarding the patients' compliance. Similarly, when the patients miss a dose, the caregiver will be notified by the mobile app, and can intervene as necessary on a real-time basis. This will further ensure the patient's adherence factor improves by such social interactive techniques via various mobile app 135 designs.

In various embodiments, pharmacists may have access to the mobile app 135 to monitor multiple patients in a secured way. The pharmacists will be able to use the mobile app 135 to establish connection with a particular patient's connected pill dispenser remotely or using NFC wireless communication method while nearby the device. This is to allow the pharmacy representative to identify him/herself to open the locked connected pill dispenser in order to replenish pills. Some embodiment app 135 implementations may also allow the pharmacists to configure medicine schedule per individual patients, and generate alerts when the patients run low on their meds supply.

In various examples, doctors may have access to an embodiment mobile app 135 to monitor individual patients, get notifications based on certain conditional threshold, visibility of the meds schedule, and ability to adjust medication on a dynamic basis.

NucleusRx RESTful APIs:

In various implementations, a set of RESTful APIs are available pharmacists to integrate NucleusRx operations with their existing application, or to allow for customization and optimization of their patient operations. The APIs may provide similar functions as available via the NucleusRx portal. In some designs, the APIs may be available for both desktop and mobile applications.

In various scenarios illustrative of some embodiments' usage, other eco-system entities, such as, doctor's office, managed care services, hospitals, rehabilitation centers, and the payers, may choose to consume NucleusRx APIs in order to have authorized and secured access to patient's medication and compliance information from remote applications.

Some exemplary APIs may also be designed for the companies interested in utilizing NucleusRX systems for clinical studies for monitoring and data gathering purpose.

Further, third party companies, working to improve overall healthcare systems, can use the APIs to access aggregated and anonymized medicine adherence and other patient related information as per regulation and patient consents.

NucleusRx Central Cloud Server:

Some embodiment NucleusRx implementations may include a cloud-based central server configured to act as a hub or the platform for the entire solution, and facilitate policy, configuration, and communication among multiple parties and user interfaces involved in the solution. In various embodiments, the NucleusRx cloud-based central server may be a healthcare regulations compliant system, which will also record patient behavior, adherence factors, and administrative records, among many other functions.

In the Summary above and in this Detailed Description, and the Claims below, and in the accompanying drawings, reference is made to particular features of various embodiments of the invention. It is to be understood that the disclosure of embodiments of the invention in this specification is intended to be interpreted as including all possible combinations of such particular features. For example, where a particular feature is disclosed in the context of a particular aspect or embodiment of the invention, or a particular claim, that feature can also be used—to the extent possible—in combination with and/or in the context of other particular aspects and embodiments of the invention, and in the invention generally.

While multiple embodiments are disclosed, still other embodiments of the present invention will become apparent to those skilled in the art from this detailed description. The invention is capable of myriad modifications in various obvious aspects, all without departing from the spirit and scope of the present invention. Accordingly, the drawings and descriptions are to be regarded as illustrative in nature and not restrictive.

It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments.

In the present disclosure, various features may be described as being optional, for example, through the use of the verb "may;" or, through the use of any of the phrases: "in some embodiments," "in some implementations," "in some designs," "in various embodiments," "in various implementations," "in various designs," "in an illustrative example," or "for example;" or, through the use of parentheses. For the sake of brevity and legibility, the present disclosure does not explicitly recite each and every permutation that may be obtained by choosing from the set of optional features. However, the present disclosure is to be interpreted as explicitly disclosing all such permutations. For example, a system described as having three optional features may be embodied in seven different ways, namely with just one of the three possible features, with any two of the three possible features or with all three of the three possible features.

In various embodiments, elements described herein as coupled or connected may have an effectual relationship realizable by a direct connection or indirectly with one or more other intervening elements.

In the present disclosure, the term "any" may be understood as designating any number of the respective elements, that is, as designating one, at least one, at least two, each or all of the respective elements. Similarly, the term "any" may be understood as designating any collection(s) of the respective elements, that is, as designating one or more collections of the respective elements, a collection comprising one, at least one, at least two, each or all of the respective elements. The respective collections need not comprise the same number of elements.

While various embodiments of the present invention have been disclosed and described in detail herein, it will be apparent to those skilled in the art that various changes may be made to the configuration, operation and form of the invention without departing from the spirit and scope thereof. In particular, it is noted that the respective features of embodiments of the invention, even those disclosed solely in combination with other features of embodiments of the invention, may be combined in any configuration excepting those readily apparent to the person skilled in the art as nonsensical. Likewise, use of the singular and plural is solely for the sake of illustration and is not to be interpreted as limiting.

In the present disclosure, all embodiments where "comprising" is used may have as alternatives "consisting essentially of," or "consisting of." In the present disclosure, any method or apparatus embodiment may be devoid of one or more process steps or components. In the present disclosure, embodiments employing negative limitations are expressly disclosed and considered a part of this disclosure.

Certain terminology and derivations thereof may be used in the present disclosure for convenience in reference only and will not be limiting. For example, words such as "upward," "downward," "left," and "right" would refer to directions in the drawings to which reference is made unless otherwise stated. Similarly, words such as "inward" and "outward" would refer to directions toward and away from, respectively, the geometric center of a device or area and designated parts thereof. References in the singular tense include the plural, and vice versa, unless otherwise noted.

The term "comprises" and grammatical equivalents thereof are used herein to mean that other components, ingredients, steps, among others, are optionally present. For example, an embodiment "comprising" (or "which comprises") components A, B and C can consist of (i.e., contain only) components A, B and C, or can contain not only components A, B, and C but also contain one or more other components.

Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

The term "at least" followed by a number is used herein to denote the start of a range beginning with that number (which may be a range having an upper limit or no upper limit, depending on the variable being defined). For example, "at least 1" means 1 or more than 1. The term "at most" followed by a number (which may be a range having 1 or 0 as its lower limit, or a range having no lower limit, depending upon the variable being defined). For example, "at most 4" means 4 or less than 4, and "at most 40%" means 40% or less than 40%. When, in this specification, a range is given as "(a first number) to (a second number)" or "(a first number)-(a second number)," this means a range whose limit is the second number. For example, 25 to 100 mm means a range whose lower limit is 25 mm and upper limit is 100 mm.

Many suitable methods and corresponding materials to make each of the individual parts of embodiment apparatus are known in the art. According to an embodiment of the present invention, one or more of the parts may be formed by machining, 3D printing (also known as "additive" manufacturing), CNC machined parts (also known as "subtractive" manufacturing), and injection molding, as will be apparent to a person of ordinary skill in the art. Metals, wood, thermoplastic and thermosetting polymers, resins and elastomers as may be described herein-above may be used. Many suitable materials are known and available and can be selected and mixed depending on desired strength and flexibility, preferred manufacturing method and particular use, as will be apparent to a person of ordinary skill in the art.

Any element in a claim herein that does not explicitly state "means for" performing a specified function, or "step for" performing a specific function, is not to be interpreted as a "means" or "step" clause as specified in 35 U.S.C. § 112 (f). Specifically, any use of "step of" in the claims herein is not intended to invoke the provisions of 35 U.S.C. § 112 (f). Elements recited in means-plus-function format are intended to be construed in accordance with 35 U.S.C. § 112 (f).

Recitation in a claim of the term "first" with respect to a feature or element does not necessarily imply the existence of a second or additional such feature or element.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim in this or any application claiming priority to this application require more features than those expressly recited in that claim. Rather, as the following claims reflect, inventive aspects may lie in a combination of fewer than all features of any single foregoing disclosed embodiment. Thus, the claims following this Detailed Description are hereby expressly incorporated into this Detailed Description, with each claim standing on its own as a separate embodiment. This disclosure is intended to be interpreted as including all permutations of the independent claims with their dependent claims.

According to an embodiment of the present invention, the system and method may be accomplished through the use of one or more computing devices. As depicted, for example, at least in FIG. 1, FIG. 2, FIG. 3, FIG. 4, FIG. 5, and FIG. 6, one of ordinary skill in the art would appreciate that an exemplary system appropriate for use with embodiments in accordance with the present application may generally include one or more of a Central processing Unit (CPU), Random Access Memory (RAM), a storage medium (e.g., hard disk drive, solid state drive, flash memory, cloud storage), an operating system (OS), one or more application software, a display element, one or more communications means, or one or more input/output devices/means. Examples of computing devices usable with embodiments of the present invention include, but are not limited to, proprietary computing devices, personal computers, mobile computing devices, tablet PCs, mini-PCs, servers or any combination thereof. The term computing device may also describe two or more computing devices communicatively linked in a manner as to distribute and share one or more resources, such as clustered computing devices and server banks/farms. One of ordinary skill in the art would understand that any number of computing devices could be used, and embodiments of the present invention are contemplated for use with any computing device.

In various embodiments, communications means, data store(s), processor(s), or memory may interact with other components on the computing device, in order to effect the provisioning and display of various functionalities associated with the system and method detailed herein. One of ordinary skill in the art would appreciate that there are numerous configurations that could be utilized with embodiments of the present invention, and embodiments of the present invention are contemplated for use with any appropriate configuration.

According to an embodiment of the present invention, the communications means of the system may be, for instance, any means for communicating data over one or more networks or to one or more peripheral devices attached to the system. Appropriate communications means may include, but are not limited to, circuitry and control systems for providing wireless connections, wired connections, cellular connections, data port connections, Bluetooth connections, or any combination thereof. One of ordinary skill in the art would appreciate that there are numerous communications means that may be utilized with embodiments of the present invention, and embodiments of the present invention are contemplated for use with any communications means.

Throughout this disclosure and elsewhere, block diagrams and flowchart illustrations depict methods, apparatuses (that is, systems), and computer program products. Each element of the block diagrams and flowchart illustrations, as well as each respective combination of elements in the block diagrams and flowchart illustrations, illustrates a function of the methods, apparatuses, and computer program products. Any and all such functions ("depicted functions") can be implemented by computer program instructions; by special-purpose, hardware-based computer systems; by combinations of special purpose hardware and computer instructions; by combinations of general purpose hardware and computer instructions; and so on-any and all of which may be generally referred to herein as a "circuit," "module," or "system."

While the foregoing drawings and description may set forth functional aspects of the disclosed systems, no particular arrangement of software for implementing these functional aspects should be inferred from these descriptions unless explicitly stated or otherwise clear from the context.

Each element in flowchart illustrations may depict a step, or group of steps, of a computer-implemented method. Further, each step may contain one or more sub-steps. For the purpose of illustration, these steps (as well as any and all other steps identified and described above) are presented in order. It will be understood that an embodiment can contain an alternate order of the steps adapted to a particular application of a technique disclosed herein. All such variations and modifications are intended to fall within the scope of this disclosure. The depiction and description of steps in any particular order is not intended to exclude embodiments having the steps in a different order, unless required by a particular application, explicitly stated, or otherwise clear from the context.

Traditionally, a computer program consists of a sequence of computational instructions or program instructions. It will be appreciated that a programmable apparatus (that is, computing device) can receive such a computer program and, by processing the computational instructions thereof, produce a further technical effect.

A programmable apparatus may include one or more microprocessors, microcontrollers, embedded microcontrollers, programmable digital signal processors, programmable devices, programmable gate arrays, programmable array logic, memory devices, application specific integrated circuits, or the like, which can be suitably employed or configured to process computer program instructions, execute computer logic, store computer data, and so on. Throughout this disclosure and elsewhere a computer can include any and all suitable combinations of at least one general purpose computer, special-purpose computer, programmable data processing apparatus, processor, processor architecture, and so on.

It will be understood that a computer can include a computer-readable storage medium and that this medium may be internal or external, removable and replaceable, or fixed. It will also be understood that a computer can include a Basic Input/Output System (BIOS), firmware, an operating system, a database, or the like that can include, interface with, or support the software and hardware described herein.

Embodiments of the system as described herein are not limited to applications involving conventional computer programs or programmable apparatuses that run them. It is contemplated, for example, that embodiments of the invention as claimed herein could include an optical computer, quantum computer, analog computer, or the like.

Regardless of the type of computer program or computer involved, a computer program can be loaded onto a computer to produce a particular machine that can perform any and all of the depicted functions. This particular machine provides a means for carrying out any and all of the depicted functions.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain or store a program for use by or in connection with an instruction execution system, apparatus, or device.

Computer program instructions can be stored in a computer-readable memory capable of directing a computer or other programmable data processing apparatus to function in a particular manner. The instructions stored in the computer-readable memory constitute an article of manufacture including computer-readable instructions for implementing any and all of the depicted functions.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

The elements depicted in flowchart illustrations and block diagrams throughout the figures imply logical boundaries between the elements. However, according to software or hardware engineering practices, the depicted elements and the functions thereof may be implemented as parts of a monolithic software structure, as standalone software modules, or as modules that employ external routines, code, services, and so forth, or any combination of these. All such implementations are within the scope of the present disclosure.

Unless explicitly stated or otherwise clear from the context, the verbs "execute" and "process" are used interchangeably to indicate execute, process, interpret, compile, assemble, link, load, any and all combinations of the foregoing, or the like. Therefore, embodiments that execute or process computer program instructions, computer-executable code, or the like can suitably act upon the instructions or code in any and all of the ways just described.

The functions and operations presented herein are not inherently related to any particular computer or other apparatus. Various general-purpose systems may also be used with programs in accordance with the teachings herein, or it may prove convenient to construct more specialized apparatus to perform the required method steps. The required structure for a variety of these systems will be apparent to those of skill in the art, along with equivalent variations. In addition, embodiments of the invention are not described with reference to any particular programming language. It is appreciated that a variety of programming languages may be used to implement the present teachings as described herein, and any references to specific languages are provided for disclosure of enablement and best mode of embodiments of the invention. Embodiments of the invention are well suited to a wide variety of computer network systems over numerous topologies. Within this field, the configuration and management of large networks include storage devices and computers that are communicatively coupled to dissimilar computers and storage devices over a network, such as the Internet.

A number of implementations have been described. Nevertheless, it will be understood that various modifications may be made. For example, advantageous results may be achieved if the steps of the disclosed techniques were performed in a different sequence, or if components of the disclosed systems were combined in a different manner, or if the components were supplemented with other components. Accordingly, other implementations are contemplated within the scope of the following claims.

What is claimed is:

1. A system for dispensing medicine to a patient, the system comprising:
    a medicine dispenser comprising:
        a processor,
        a memory operably coupled with the processor, wherein the memory encodes processor executable program instructions and data to program and configure the processor to control the medicine dispenser,
a plurality of object bins supported in respective openings positioned in a dispensing tray, wherein the plurality of object bins comprises circular bins of varied diameters that are positioned at varied distances from a center of the dispensing tray,
a robotic arm configured to extend and retract in a direction perpendicular to a plane of the dispensing tray, the robotic arm having a gripper positioned at a distal end configured to grip a pill from at least one of the plurality of object bins, and
a dispensing chute positioned on the dispensing tray, wherein a relative 360-degree motion along a horizontal plane between the dispensing tray and the robotic arm positions the dispensing chute below the robotic arm, wherein the robotic arm is configured to release the pill into the dispensing chute,
an image sensor, and
a biometric sensor; and
a software program product configured to communicate with a pharmacy server of a pharmacy; a physician server of a prescribing physician of the patient; a caregiver device; patient selected third parties; a user device of the patient; and one or more patient sensor operably couplable with the processor to sense and communicate patient data associated with the patient;
wherein the software program product is configured to:
transfer the patient data sensed and communicated by the one or more patient sensor to at least one of the pharmacy server and the physician server;
update a prescription data based on the patient data; and
control the medicine dispenser with at least one of the pharmacy server and the physician server to deliver a dose to the patient based on the prescription data, wherein the dose is delivered upon authentication of an authorized user via either or both of the image sensor or the biometric sensor, wherein the authorized user is selected from the patient or an authorized caregiver.

2. The system of claim 1, wherein the software program product is configured to determine a patient condition as a function of the patient data acquired from the one or more patient sensor; wherein audio communication, video communication, or both between the physician server and the user device is initiated when the patient data indicates that the patient missed the dose.

3. The system of claim 1, wherein the software program product is configured to determine a patient condition as a function of data acquired from a healthcare professional.

4. The system of claim 1, wherein the software program product is configured to adjust the dose in response to input received from a healthcare professional.

5. The system of claim 1, wherein:
the user device of the patient and one of the one or more patient sensor is wirelessly connectable to the medicine dispenser; and
audio communication, video communication, or both between the physician server and the user device is via a secured channel for communication.

6. The system of claim 1, wherein:
one of the one or more patient sensor is a physiological sensor; and
the user device is selected from the group consisting of a smartphone, a tablet, and a digital touchscreen interface of the medicine dispenser.

7. The system of claim 6, wherein the physiological sensor is a blood-pressure sensor, blood sugar sensor, blood oxygen level sensor, heart rate sensor, temperature sensor, electrocardiogram, or combination thereof.

8. The system of claim 1, wherein the software program product is configured to determine a patient condition based on input received from the patient.

9. The system of claim 1, wherein the software program product is configured to change the dose of the medicine dispenser if the patient data indicates a condition of the patient has worsened.

10. The system of claim 9, wherein the dose adjustment is constrained within programmed dose limits.

11. The system of claim 10, wherein the programmed dose limits are set by the prescribing physician who provides the prescription data via the physician server to the pharmacy server.

12. The system of claim 1, wherein the software program product is configured to determine whether or not to send an alert to the prescribing physician via the physician server, the caregiver device, or the patient selected third party based on comparing the patient data to a reference data.

13. The system of claim 1, wherein the image sensor is configured to capture images of patient medication consumption activity, wherein the captured images are analyzed by the medicine dispenser to identify images that correlate with image data representative of various patient activity states associated with medication adherence, and wherein the captured images are time stamped based on time of capture to validate timing of medication adherence.

14. The system of claim 10, wherein the programmed dose limits are set by the prescribing physician who provides the prescription data via the physician server to the medicine dispenser, the pharmacy server, or both the medicine dispenser and the pharmacy server.

15. A system for dispensing medicine to a patient, comprising:
a processor;
a medicine dispenser comprising:
an image sensor operably coupled with the processor and configured to capture images of patient medication consumption activity, wherein the captured images are analyzed by the processor to identify images that correlate with image data representative of various patient activity states associated with medication adherence, and wherein the captured images are time stamped based on time of capture to validate timing of medication adherence,
a dispensing tray comprising a dispensing chute and a plurality of object bins positioned in respective openings in the dispensing tray, wherein the plurality of object bins comprises circular bins of varied diameters that are positioned at varied distances from a center of the dispensing tray, and
a robotic arm having a gripper at a distal end configured to grip pills from that at least one of the plurality of object bins, wherein a relative 360-degree motion along a horizontal plane between the dispensing tray and the robotic arm positions the dispensing chute below the robotic arm, and wherein robotic arm is configured to extend and retract in a direction perpendicular to a plane of the dispensing tray to grip pills from at least one of the plurality of object bins and dispense pills to the dispensing chute; and
a memory operably coupled with the processor, wherein the memory encodes processor executable program instructions and data to program and configure the processor to control the medicine dispenser;

wherein the processor and the memory are configured to:
- transfer patient data sensed and communicated by one or more patient sensor to at least one of a physician server and a pharmacy server;
- update a prescription data using the pharmacy server based on a physician directive data of the prescribing physician sent from the physician server to the pharmacy server;
- control the medicine dispenser with (i) the pharmacy server to deliver a dose to the patient based on the prescription data, (ii) the physician server to adjust the dose, or both (i) and (ii);
- determine medication adherence of the patient to the prescription data based on the patient data; and
- automatically initiate communication between the physician server of the prescribing physician and the user device of the patient when the determined medication adherence based on the sensed patient data indicates that the patient missed the dose.

16. The system of claim 15, wherein:
the user device is wirelessly connectable to the medicine dispenser; and
the software program product is configured to send an encouraging message to the user device of the patient based on the determined medication adherence exceeding a predetermined target.

17. The system of claim 15, wherein one of the one or more patient sensor is a physiological sensor.

18. The system of claim 17, wherein the physiological sensor is a blood-pressure sensor, blood sugar sensor, blood oxygen level sensor, heart rate sensor, temperature sensor, electrocardiogram, or combination thereof.

19. The system of claim 15, wherein the software program product is configured to, in response to determining a lack of medication adherence, send a notification of the lack of medication adherence to one or more of the pharmacy server, the physician server, the caregiver device, and patient selected third parties.

20. The system of claim 19, wherein the software program product is configured to send the notification to the prescribing physician via the physician server, the caregiver device, or both.

21. The system of claim 15, wherein at least one of the one or more patient sensor is wirelessly connectable to the medicine dispenser.

22. The system of claim 15, wherein at least one of the one or more patient sensor is an activity sensor.

23. The system of claim 15, wherein the software program product is configured to adjust one or more subsequent dose depending upon drug type.

24. The system of claim 15, the software program product is configured to adjust one or more subsequent dose by increasing an amount of drug included in at least one subsequent dose.

25. The system of claim 15, wherein the robotic arm is configured to rotate over the plurality of object bins.

26. The system of claim 15, wherein the gripper is a vacuum suction gripper including a tube-shaped rubber skirt.

27. The system of claim 15, wherein the processor executable program instructions are configured for communication with a user device of a doctor to transfer the prescription data from the user device of the doctor to the pharmacy server of the pharmacy.

28. The system of claim 15, wherein the processor executable program instructions are configured for communication with a caregiving server to transfer payment to the pharmacy server of the pharmacy.

* * * * *